US006942865B2

(12) United States Patent
Estes et al.

(10) Patent No.: US 6,942,865 B2
(45) Date of Patent: *Sep. 13, 2005

(54) METHODS AND REAGENTS TO DETECT AND CHARACTERIZE NORWALK AND RELATED VIRUSES

(75) Inventors: Mary K. Estes, Houston, TX (US); Xi Jiang, Virginia Beach, VA (US); David Y. Graham, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/314,739

(22) Filed: Dec. 9, 2002

(65) Prior Publication Data

US 2003/0129588 A1 Jul. 10, 2003

Related U.S. Application Data

(63) Continuation of application No. 08/486,049, filed on Jun. 7, 1995, now Pat. No. 6,572,862, which is a continuation of application No. 07/696,454, filed on May 6, 1991, now abandoned, and a continuation-in-part of application No. 07/573,509, filed on Aug. 27, 1990, now abandoned, and a continuation-in-part of application No. 07/515,933, filed on Apr. 27, 1990, now abandoned, which is a continuation-in-part of application No. 07/433,492, filed on Nov. 8, 1989, now abandoned.

(51) Int. Cl.$^7$ .................... A61K 39/00; A61K 39/38; A61K 39/12; A61K 38/00; A61K 39/295
(52) U.S. Cl. .................... 424/204.1; 424/184.1; 424/139.1; 424/202.1; 424/199.1; 424/196.11; 514/2; 530/350
(58) Field of Search .................... 424/184.1, 204.1, 424/196.11, 199.1, 202.1, 139.1; 530/350; 514/2

(56) References Cited

U.S. PATENT DOCUMENTS

| | | | | |
|---|---|---|---|---|
| 4,358,535 A | | 11/1982 | Falkow et al. | |
| 4,751,080 A | | 6/1988 | Wyatt et al. | |
| 4,814,268 A | | 3/1989 | Kreider et al. | |
| 5,559,014 A | * | 9/1996 | Estes et al. | 435/91.2 |
| 5,861,241 A | * | 1/1999 | Herrmann et al. | 435/5 |
| 6,156,883 A | * | 12/2000 | Estes et al. | 530/389.4 |
| 6,210,682 B1 | * | 4/2001 | Estes et al. | 424/215.1 |
| 6,572,862 B1 | * | 6/2003 | Estes et al. | 424/204.1 |
| 6,593,080 B1 | * | 7/2003 | Smith | 435/5 |
| 6,673,355 B1 | * | 1/2004 | Estes et al. | 424/215.1 |
| 6,696,562 B1 | * | 2/2004 | Schultz-Cherry et al. | 536/23.72 |
| 2003/0091593 A1 | * | 5/2003 | Bachmann et al. | 424/204.1 |
| 2003/0099668 A1 | * | 5/2003 | Bachmann et al. | 424/204.1 |
| 2003/0129588 A1 | * | 7/2003 | Estes et al. | 435/5 |

FOREIGN PATENT DOCUMENTS

| | | | | |
|---|---|---|---|---|
| WO | WO 91/07502 | * | 5/1991 | C12N/15/33 |
| WO | WO 94/05700 | * | 3/1994 | C07K/15/00 |
| WO | WO 03/101176 A2 | * | 12/2003 | |

OTHER PUBLICATIONS

Alberts, B., et al; Molecular Biology of the Cell, Second Edition; Chapter 5; Basic Genetic Mechanisms, 258–266 (1989).

Alberts, B., et al.; Molecular Biology of the Cell, Third Edition; The functional properties of antibodies, pp. 1211–1227 (1994).

Appleton, H.; "Small round Viruses: Classification and Role in Food–Borne Infections," in Novel Diarrhoea Viruses (Ciba Found Symp), 128: 108–125, 1987.

Ball, J. M., et al.; Recombinant Norwalk virus–like particles given orally to volunteers: phase I study; Gastroenterology 117 (1): 40–48, Jul. 1999.

Ball, J.M., et al.; Oral immunization with recombinant Norwalk virus–like particles induces a systemic and mucosal immune response in mice; J Virol 72 (2): 1345–1353, Feb. 1998.

Benjamini, E., et al.; Immunology: A Short Course; Second Edition, pp 174–175 (1991).

(Continued)

Primary Examiner—N. M. Minnifield
(74) Attorney, Agent, or Firm—Fulbright & Jaworski, LLP

(57) ABSTRACT

Double-stranded cDNA was synthesized from nucleic acid extracted from Norwalk virus purified from stool specimens of volunteers. One clone was isolated from a cDNA library constructed in a pUC-13 vector after amplification of the cDNA. The specificity of this cDNA (pUCNV-953) was shown by hybridization assays. The cDNA reacted with post (but not pre-) infection stool samples from Norwalk volunteers and with highly purified Norwalk virus, but not with other common enteric viruses such as hepatitis A virus and rotavirus. Finally, the probe detected virus in the same fractions of CsCl gradients in which viral antigen was detected using a specific Norwalk virus radioimmunoassay, and particles were detected by immune electron microscopy. Single-stranded RNA probes derived from the DNA clone after subcloning into an in vitro transcription vector were also used to show that the Norwalk virus contains a ssRNA genome of about 8 kb in size. The original clone was also used to detect additional cDNAs which represent at least 7 kb of nucleic acid of the Norwalk genome. The availability of a Norwalk-specific cDNA and the first partial genome sequence information allow rapid cloning of the entire genome and of establishment of sensitive diagnostic assays. Such assays can be based on detection of Norwalk virus nucleic acid or Norwalk viral antigen using polyclonal or monoclonal antibodies to proteins expressed from the cDNA or to synthetic peptides made based on the knowledge of the genome sequence. Assays using proteins deduced from the Norwlk virus genome and produced in expression systmes can measure antibody responses. Vaccines made by recombinant DNA technology are now feasible.

8 Claims, 16 Drawing Sheets

OTHER PUBLICATIONS

Black, R.E., et al.; Acquisition of serum antibody to Norwalk Virus and rotavirus and relation to diarrhea in a longitudinal study of young children in rural Bangladesh; J Infect Dis 145 (4): 483–489, Apr. 1982.

Brinker, J. P., et al.; Detection of Norwalk virus and other genogroup 1 human calciviruses by a monoclonal antibody, recombinant–antigen–based immunoglobulin M capture enzyme immunoassay; J Clin Microbiol 36 (4): 1064–1069, Apr. 1998.

Brock and Madigan; Biology of Microorganisms, 6th Edition, pp. 843; 1991.

Caul, E. O., et al.; The electron microscopical and physical characteristics of small round human fecal viruses: an interim scheme for classification; J Med Virol 9 (4):257–265, 1982.

Chou, P., et al.; Prediction of the secondary structure of proteins from their amino acid sequence; Neo Enziymology 47: 45–148 (1978).

Cubitt, W. D., et al.; Antigenic relationships between human calciviruses and Norwalk virus; J Infect Dis 156 (5): 806–814, Nov. 1987.

Dingle, J.H., et al.; Am J Hyg., 58: 16–30 (1953).

Dolin, R., et al.; Biological properties of Norwalk and agent of acute infectious nonbacterial gastroenteritis; Proc Soc Exp Biol Med, 140 (2): 578–583, Jun. 1972.

Dolin, R., et al.; Transmission of acute infectious nonbacterial gastroenteritis to volunteers by oral administration of stool filtrates; J Infect Dis 123 (3): 307–312, Mar. 1971.

Dresser; Ch. 8 of "Handbook of Experimental Immunochemistry", Weir, et al.; Blackwell Publ v. 1:8.1–8.21, 1986.

DuPont, H. L.; Consumption of raw shellfish—is the risk now unacceptable?; N Engl J Med 314 (11): 707–708, Mar. 13, 1986.

Estes, M. K., et al.; Norwalk virus vaccins: challenges and progress; J Infect Dis 181 (2): S367–S373, May 2000.

Fields, B. N., et al.; Immunization against virus disease; Fields Virology, vol. 1, Third Edition, pp. 467, 475, 795; 1996.

Geysen, M., et al., Use of peptide synthesis to probe viral antigens for epitopes to a resolution of a single amino acid; Proc. Natl. Acad. Sci. USA 81: 3998–4002 (1984).

Glass, P. J., et al.; Norwalk virus open reading frame 3 encodes a minor structural protein; J Virol 74 (14): 6581–6591, Jul. 2000.

Greenberg, H.B., et al.; Proteins of Norwalk virus; J Virol 37 (3): 994–999, Mar. 1981.

Greenberg, H. B., et al.; Solid–phase microtiter radioimmunoassay for detection of the Norwalk strain of acute nonbacterial, epidemic gastroenteritis virus and its antibodies; J Med Virol 2 (2): 97–108, 1978.

Hale, A. D., et al.; Expression and self–assembly of Grimsby virus: antigenic distinction from Norwalk and Mexico viruses; Clin Diagn Lab Immunol 6 (1): 142–145, Jan. 1999.

Harlow, E., et al.; Antibodies: A laboratory manual; 115, 141, 156–157, 242 (1988).

Janeway, Charles A., Jr., et al.; Immuno Biology The Immune System in Health and Disease, Fourth Edition, pp. 602–603, 1999.

Janeway, C. A., et al.;.Immuno Biology: The Immune System in Health and Disease; Fourth Edition, pp. 99–100.

Janeway, C. A., et al.; Immunobiology: The Immune System in Health and Disease, 4th Edition, pp 594, 603; 1999.

Jiang, X., et al.; Sequence and genomic organization of Norwalk virus; Virology 195 (1): 51–61, Jul. 1993.

Jiang, X., et al., Norwalk virus genome cloning and characterization; Science, 250 (4987): 1580–1583, Dec. 14, 1990.

Jiang, X., et al.; Detection of Norwalk virus in stool by polymerase chain reaction; J Clin Microbiol, 30 (10): 2529–2534, Oct. 1992.

Johnson, P., et al.; Multiple–challenge study of host susceptibility to Norwalk Gastroenteritis in US adults; J Infect Dis 161: 18–21 (1990).

King, Diana J., et al.; Toxicity of Polyacrylamide and Acrylamide Monomer; Review on Environmental Health, vol. VIII (1–4), 3–16, 1989.

Kwok, A.Y.C., et al.; Species identification and phylogenetic relationships based on partial HSP60 gene sequences within the genus Staphylococcus; Int J Syst Bacteriol 49 (Pt3): 1181–1192, Jul. 1999.

Liang, O. D., et al.; Isolation and characterization of a vitronectin–binding surface protein from *Staphylococcus aureus;* Biochim Biophys Acta 1250 (1): 110–116, Jul. 3, 1995.

Mandal, C., et al.; Production of highly specific polyclonal and monoclonal antibodies using estradiol–3–O–carboxymethyl ether as hapten; Steroids 52/5 & 6, 551–560, Nov. and Dec. 1998.

Margalilt, H., et al.; Prediction of immunodominant helper T cell antigenic sites from the primary sequence; The Journal of Immunology 138: 2213–2229 (1987).

Matsui, S. M., et al.; The isolation and characterization of a Norwalk virus–specific cDNA; J Clin Invest 87 (4): 1458–1461, Apr. 1991.

Nakata, S., et al.; Humoral immunity in infants with gastroenteritis caused by human calicivirus; J Infect Dis 152: 274–279 (1985).

Noel, J. S., et al.; correlation of patient immune responses with genetically characterized small round–structured viruses involved in outbreaks of nonbacterial acute gastroenteritis in the United States, 1990 to 1995; J Med Virol 53 (4): 372–383, Dec. 1997.

Norcott, J. P., et al.; Genomic diversity of small round structured viruses in the United Kingdom; J Med Virol 44 (3): 280–286, Nov. 1994.

Parker, J., et al.; New hydrophilicity scale derived from high–performance liquid chromatography peptide retention date: Correlation of predicted surface residues with antigenicity and x–ray–derived accessible sites; Biochemistry 25: 5425–5432 (1986).

Parrino, T., et al.; Clinical immunity in acute gastroenteritis caused by Norwalk agent; N Engl J Med 297 (2): 86–89, Jul. 14, 1977.

Phonimdaeng, P., et al.; Molecular cloning and expression of the coagulase gene of *Staphylococcus aureus* 8325–4;J Gen Microbiol, 134 (Pt 1): 75–83, Jan. 1988.

Pickering, L. K., et al.; Active Immunization, 2000 Red Book; Report of the Committee on Infectious Diseases; Twenty–Fifth Edition; pp 16–28, 2000.

Plana–Duran, J., et al.; Oral immunization of rabbits with VP60 particles confers protection against rabbit hemorrhagic disease; Arch Virol 141 (8): 1423–1436, 1996.

Ploegh, H. L., et al.; Molecular cloning of human histocompatibility antigen cDNA fragment; Proc Natl Acad Sci USA 77 (10): 6081–6085, Oct. 1990.

Prasad, B. V., et al.; X-ray crystallographic structure of the Norwalk virus capsid; Science 286 (5438): 287–290, Oct. 8, 1999.

Research Sheet; Calbiochem, Pansorbin Cells, Jun. 23, 1997.

Roitt, E. M., et al.; Immunology, 1989.

Rouch, D. A., et al.; The aacA–aphD gentamicin and kanamycin resistance determinant of Tn4001 from *Staphylococcus aureus:* expression and nucleotide sequence analysis; J Gen Microbiol 133 (Pt 11): 3039–3052, Nov. 1987.

Ryder, R., et al.; Evidence of immunity induced by naturally acquired Rotavirus and Norwalk virus infection on two remote panamanian islands; J Infect Dis 151: 99–105 (1985).

Tanaka, T., et al.; High yield production of monoclonal antibodies to recombinant Norwalk virus–like particles by oral immunization; Presented at CDC meeting.

Treanor, J., et al.; Production of a monoclonal antibody against the Snow Mountain agent of gastroenteritis by in vitro immunization of murine spleen cells; Proc Natl Acad Sci USA 85 (10): 3613–3617, May 1988.

Uhlen, M., et al.; Complete Sequence of the Staphylococcal Gene Encoding Protein A. A Gene Evolved Through Multiple Duplications; J Biol Chem. 259 (3): 1695–1702, Feb. 10, 1984.

Walter, G.; Production and use of antibodies against synthetic peptides; J Immunol Methods 88 (2): 149–161, Apr. 17, 1986.

Wang, J., et al.; Sequence diversity of small, round–structured viruses in the Norwalk virus group; J Virol 68 (9): 5982–5990, Sep. 1994.

Ward, R., et al.; Viral Gastroenteritis Vaccines; Mucosal Immunology, Chapter 54, 867–880 (1999).

Wang, J., et al.; Sequence diversity of small, round–structured viruses in the Norwalk virus group; J Virol, 68 (9): 5982–5990, Sep. 1994.

White, L. J., et al.; Biochemical characterization of a smaller form of recombinant Norwalk virus capsids assembled in insect cells; J Virol 71 (10): 8066–8072, Oct. 1997.

Yamada, S., et al.; An autolysin ring associated with cell separation of *Staphylococcus aureus;* J Bacteriol 178 (6): 1565–1571, Mar. 1996.

* cited by examiner

| Test clone | Patient stool sample 1b 2b 1a 2a | Hybridization temperature |
|---|---|---|
| pUC-27 | · ● · ● | 50° |
|  | · ● | 65° |
| pUC-593 | ● · ● | 50° |
| | ● ● | 65° |
| pUC-13 | ● ● · ● | 50° |
| | ● ● | 65° |
| pUCNV-953 | · ● | 50° |
| |  | 65° |

FIG. 2A

```
                                          21                             41
Seq. ID. NO. 5 - G TGC TCT GGG AGC GGG CAT ACA GGT TGG TGG CGA CAG GCC CTC CAA
Seq. ID. NO. 6 -   cys ser gly ser gly his thr gly trp trp arp gin ala leu gin
                          61                            81
                  AGC CAA AGG TAT CAA CAA AAT TTG CAA CTG CAA GAA AAT TCT TTT
                  ser gin arg tyr gin gin asn leu gin leu gin glu asn ser phe
                          101                           121
                  AAA CAT GAC AGG GAA ATG ATT GGG TAT CAG GTT GAA GCT TCA AAT
                  lys his asp arg glu met ile gly tyr gln val glu ala ser asn
                          141                           161                 18
                  CAA TTA TTG GCT AAA AAT TTG GCA ACT AGA TAT TCA CTC CTC CGT
                  gin leu leu ala lys asn leu ala thr arg tyr ser leu leu arg
                  1                             201                         221
                  GCT GGG GGT TTG ACC AGT GCT GAT GCA GCA AGA TCT GTG GCA GGA
                  ala gly gly leu thr ser ala asp ala ala arg ser val ala gly
                                          241                           261
                  GCT CCA GTC ACC CGC ATT GTA GAT TGG AAT GGC GTG AGA GTG TCT
                  ala pro val thr arg ile val asp trp asn gly val arg val ser
                                  281                           301
                  GCT CCC GAG TCC TCT GCT ACC ACA TTG AGA TCC GGT GGC TTC ATG
                  ala pro glu ser ser ala thr thr leu arg ser gly gly phe met
                          321                           341                 36
                  TCA GTT CCC ATA CCA TTT GCC TCT AAG CAA AAA CAG GTT CAA TCA
                  ser val pro ile pro phe ala ser lys gin lys gin val gin ser
                  1                           381                         401
                  TCT GGT ATT AGT AAT CCA AAT TAT TCC CCT TCA TCC ATT TCT CGA
                  ser gly ile ser asn pro asn tyr ser pro ser ser ile ser arg
                                          421                           441
                  ACC ACT AGT TGG GTC GAG TCA CAA AAC TCA TCG AGA TTT GGA AAT
                  thr thr ser trp val glu ser gin asn ser ser arg phe gly asn
                                  461                           481
                  CTT TCT CCA TAC CAC GCG GAG GCT CTC AAT ACA GTG TGG TTG ACT
                  leu ser pro tyr his ala glu ala leu asn thr val trp leu thr
                          501
                  CCA CCC GGT TCA ACC
                  pro pro gly ser thr
```

FIG. 5

```
SEQ. ID. NO. 7   NV     HFDADYTAVDSTONROIMT--ESFSIHSR--LTASPEL-AEVVAQDLLAPSEHDV------GDYVIRVK--EG-LPSGFPCTSQVN
SEQ. ID. NO. 8   HEV    VFENDFSEFDSTONNFSLG-LECAIMEEC-GMPQWLI-RLYHLIRSAVILQAPKESLR-GFVKKH------S-KHSGEPGTLLVN
SEQ. ID. NO. 9   HCV    GFSYDTRCFDSTVTESDIR-TEEAIYQCCDLDPQARV-AIKSLTERLYVGGPLTNSR-GENCGYRRCRAS-RASGVLTTSCGN
SEQ. ID. NO. 10  HAV    GLDLDFSAFDASLSPFMIREAGRINSELS-GTPSHFGTALINTIYSKHLLYNCCYHVCGS------------MPSGSPCTALLN
SEQ. ID. NO. 11  JE     MYADDTAGWDTRITRTDLE-NEAKVLELLDGEHRMLARAIIELTYRHKVVKVMRPAAE-GKTVMDVISREDQRGSGQVVTYALN
SEQ. ID. NO. 12  POLIO  FA--FDYTGYDASLS-PAWFEAL-KHVLEKIGFGDRVDY-IDYLNHSHHLYKNKTYCVKGG------------MPSGCSGTSIFN
SEQ. ID. NO. 13  FMD    VWDVDYSAFDANHCSDAWNIMFEEVFRTDF GFHPNAEWILKTLVNTEHAYENKRITV-EGG------------MPSGCSATSIIN
SEQ. ID. NO. 14  EMC    VYDVDYSNFDSTHSVAMFRLLAEEFTPENGF-DPLTREYLESLAISTHAFEEKRFLITGG------------LPSIGCAATSHLN
SEQ. ID. NO. 15  SNBV   VLETDIASFDKS-QDDAMALTGLMILEDL-GVDQPLLDLIECAFGEISSTHLPGTGRFKFGA--H-------MKSGMFLTLFVN
SEQ. ID. NO. 16  TMV    VLELDISKYDKS-QNEFHCAVEYEIVRRL-GFEDFLGEVMKQG-HRKTTLK-DITA-GYKTC---IVY----QRKSGDVTTFIGN
SEQ. ID. NO. 17  AMV    FKEIDFSKFDKS-QNELHLHLIQERFLKYL-GIPNEFLTLVFNA--HRKSRIS--DSKN--GVFFN-VDF--QRRTGDALTYLGN
SEQ. ID. NO. 18  BMV    FLEADLSKFDKS-QGELHLEFOREILLAL-GFPAPLINWVSDF--HRDSYLS--DPHAKVGMS--VSF----QRRTGDAFTYFGN
SEQ. ID. NO. 19  CpMV   VLCCDYSSFDGLLSKQVHDVIASHINELCGGE-DDLKNARRNLMACCSRLAICKNTVVRVECG---------IPSGFPMTVIVN

SEQ. ID. NO. 7   NV     SINHVIITLCALSEATGLSPD--------------VVQSMSYFSFYGDEIVS----TDIDFDP-ARLTQILK--E
SEQ. ID. NO. 8   HEV    TVNMAVITHC-------------------------YDFRDFQVAAFKGDSIVL-CSEYRQSPG--A-A--VLIAGC
SEQ. ID. NO. 9   HCV    TLTCYIKARAACRAAGLQDCTMLVC----------GDLVVI-CESAGVQED---A-A--SL-RAF
SEQ. ID. NO. 10  HAV    SIINVNLYVFSKI-----------------FGKSPVFFCQALKILCYGDDVLIV-FSRDVQIDNLDLIGQKIVDEF
SEQ. ID. NO. 11  JE     TFTNIAVGLVRLMEAEGVIGPQHLEQLPRKTKIAVRTWLFENGEERVTRMAISGDDCVVK------PLDDRFATALHFL-NAM
SEQ. ID. NO. 12  POLIO  SMINNLIIRTLLLKTYKGID--------------LDHLKMIAYGDDVIAS----YPHEVDAS------LLAQS
SEQ. ID. NO. 13  FMD    TILNNIYVLYALRRHYEGVE--------------LDTYTMISYGDDIVVA----SDYDLDF---EASLAKTG
SEQ. ID. NO. 14  EMC    TIMNNIIIRAGLYLTYKNFE--------------FDDVKVLSYGDDLLVA----TNYQLDFDKV-RASLAKTG
SEQ. ID. NO. 15  SNBV   TVLNVVIASRVLE---------------------ERLKTSRCAAFIGDNIIH----GVVSDKEMAERCATWL-N
SEQ. ID. NO. 16  TMV    TVIIAACLASML---------------PMEKIIKGAFCGDDSLLY-FPKGCEFPDVQHSAN-LMWNFE
SEQ. ID. NO. 17  AMV    TIVTLACLCHVYDLM-----------DPNVKFVVASGDDSLIG--TVEELPRDDEF-LFTTLFNLE
SEQ. ID. NO. 18  BMV    TLVTMANIAYASDLS----------DCDCAIFSGDDSLII--SKVKPVLDTDM--FTSLFNME
SEQ. ID. NO. 19  CpMV   SIFNEILIRYHYKKLMREQQAPE---LHVQSFDKLIGLVTYGDDNLISVNAVTPYFDGKKL-KQSLAQGG
```

FIG 8

METHODS AND REAGENTS TO DETECT AND CHARACTERIZE NORWALK AND RELATED VIRUSES

This application is a continuation of U.S. application Ser. No. 08/486,049 filed Jun. 7, 1995 issued as U.S. Pat. No. 6,572,862, which is a continuation of U.S. application Ser. No. 07/696,454 filed May 6, 1991 (now abandoned), which is a continuation in part of U.S. application Ser. No. 07/433,492 filed Nov. 8, 1989 (now abandoned), U.S. application Ser. No. 07/515,933, filed Apr. 27, 1990 (now abandoned), and U.S. application Ser. No. 07/573,509 filed Aug. 27, 1990 (now abandoned).

This invention is supported in part through grants or awards from the Food and Drug Administration and the National Institute of Health.

FIELD OF THE INVENTION

The present invention relates generally to synthesizing clones of Norwalk virus and to making probes to Norwalk and related viruses. It also relates to methods of detection and characterization of Norwalk and related viruses.

BACKGROUND OF THE INVENTION

Norwalk virus is one of the most important viral pathogens causing acute gastroenteritis, the second most common illness in the United States (Dingle et al., 1953; Kapikian and Chanock, 1985). Up to 42% of cases of viral gastroenteritis have been estimated to be caused by Norwalk or Norwalk-like viruses (Kaplan et al., 1982). Both water and foodborne transmission of Norwalk virus has been documented, and particularly large epidemic outbreaks of illness have occurred following consumption of contaminated shellfish including clams, cockles, and oysters (Murphy et al., 1979; Gunn et al., 1982; Wilson et al., 1982; Gill et al., 1983; DuPont 1986; Morse et al., 1986; Sekine et al., 1989). An increase in fish and shellfish-related food poisonings has recently been noted and attributed to increased recognition of these entities by clinicians as well as to increased consumption of seafood (Eastaugh and Shepherd, 1989). Norwalk virus was discovered in 1973. However, knowledge about the virus has remained limited because it has failed to grow in cell cultures and no suitable animal models have been found for virus cultivation. Human stool samples obtained from outbreaks and from human volunteer studies, therefore, are the only source of the virus. Still the concentration of the virus in stool is usually so low that virus detection with routine electron microscopy is not possible (Dolin et al., 1972; Kapikian et al., 1972; Thornhill et al., 1975). Current methods of Norwalk virus detection include immune electron microscopy and other immunologic methods such as radio immunoassays (RIAs) or a biotin-avidin enzyme linked immunoabsorbent assays (ELISAs) which utilize acute and convalescent phase serum from humans. To date, no hyperimmune serum from animals has been successfully prepared due either to insufficient quantities or unusual properties of the viral antigen. Preliminary biophysical characterization of virions has indicated particles contain one polypeptide (Greenberg et al., 1981), but efforts to characterize the viral genome have failed. Therefore, these viruses have remained unclassified.

CITED AND RELEVANT INFORMATION

1. Dingle J, Badger G, Feller A et al. 1953. A study of illness in a group of Cleveland families: 1. Plan of study and certain general observations. Am. J. Hyg. 58:16–30.
2. Dolin R, Blacklow N R, DuPont H, Buscho R F, Wyatt R G, Kasel J A, Hornick R, and Chanock R M. 1972. Biological properties of Norwalk agent of acute infectious nonbacterial gastroenteritis. Proc. Soc. Exp. Med. and Biol. 140:578–583.
3. Dolin R, Blacklow N R, DuPont H, Formal S, Buscho R F, Kasel J A, Chames R P, Hornick R, and Chanock R M. 1971. Transmission of acute infectious nonbacterial gastroenteritis to volunteers by oral administration of stool filtrates. J. Infect. Dis. 123:307–312.
4. DuPont H L. 1986. Consumption of raw shellfish—is the risk now unacceptable? New Engl. J. Med. 314:707–708.
5. Eastaugh J, Shepherd S. 1989. Infectious and toxic syndromes from fish and shellfish consumption. Arch. Intern. Med. 149:1735–1740.
6. Gill O N, Cubitt W D, McSwiggan D A, Watney B M and Bartlett C L R. 1983. Epidemic of gastroenteritis caused by oysters contaminated with small round structured virus. Br. Med. J. 287:1532–1534.
7. Greenberg H B, Valdesuso J R, Kalica A R, Wyatt R G, McAuliffe V J, Kapikian A Z and Chanock R M. 1981. Proteins of Norwalk virus. J. Virol. 37: 994–999.
8. Gunn R A, Janowski H T, Lieb S, Prather E C, and Greenberg H B. 1982. Norwalk virus gastroenteritis following raw oyster consumption. Am. J. Epidemiol. 115:348–351.
9. Jiang X, Estes M K, and Metcalf T G. 1989. In situ hybridization for quantitative assay of infectious hepatitis A virus. J. Clin. Microbiol. 27:874–879.
10. Jiang X, Estes M K, and Metcalf T G. 1987. Detection of hepatitis A virus by hybridization with single-stranded RNA probes. Appl. Environ. Microbiol. 53:2487–2495.
11. Jiang X, Estes M K, Metcalf T G, and Melnick J L. 1986. Detection of hepatitis A virus in seeded estuarine samples by hybridization with cDNA probes. Appl. Environ. Microbiol. 52:711–717.
12. Kapikian A Z and Chanock R M. 1990. Norwalk group of viruses. In: B N Fields (ed.) Virology, Raven Press, New York, pp. 671–693.
13. Kapikian A Z, Wyatt R G, Dolin R. Thornhill T S, Kalica A R, and Chanock R M. 1972. Visualization by immune electron microscopy of a 27-nm particle associated with acute infectious nonbacterial gastroenteritis. J. Virol. 10:1075–1081.
14. Kaplan J, Feldman R, Campbell D et al. 1982. Epidemiology of Norwalk Gastroenteritis and the Role of Norwalk Virus in Outbreaks of Acute Nonbacterial Gastroenteritis. Ann. Internal Med. 96(6): 756–761.
15. Morse D L, Guzewich J J, Hanrahan J P, Stricof R, Shayegani M, Deibel R, Grabau J C, Nowak N A, Herrmann J E, Cukor G, and Blacklow NR. 1986. Widespread outbreaks of clam and oyster-associated gastroenteritis: role of Norwalk virus. New Engl. J. Med. 314:678–681.
16. Murphy A M, Grohmann G S, Christopher P J, Lopez W A, Davey G R, and Millsom R H. 1979. An Australia-wide outbreak of gastroenteritis from oysters caused by Norwalk virus. Med. J. Aust. 2:329–333.
17. Sekine S, Okada S, Hayashi Y, Ando T, Terayama T, Yabuuchi K, Miki T, and Ohashi M. 1989. Prevalence of small round structured virus infections in acute gastroenteritis outbreaks in Tokyo. Microbiol. Immunol. 33:207–217.
18. Thornhill T S, Kalica A R, Wyatt R G, Kapikian A Z, and Chanock R M. 1975. Pattern of shedding of the Norwalk particle in stools during experimentally induced gastroenteritis in volunteers as determined by immune electron microscopy. J. Infect. Dis. 132:28–34.
19. Wilson R, Anderson M J, Holman R C, Gary G W, and Greenberg H B. 1982. Waterborne gastroenteritis due to the Norwalk agent: clinical and epidemiologic investigation. Am. J. Public Health 72:72–74.
20. Hayashi Y, Ando T, Utagawa E, Sekine S, Okada S, Yabuuchi K, Miki T, and Ohashi M. 1989. Western Blot (Immunoblot) Assay, Round-Structured Virus Associated with an Acute Gastroenteritis Outbreak in Tokyo. J. Clin. Microbiol. 27:1728–1733.
21. U.S. Pat. No. 4,358,535, issued Nov. 9, 1982, to Fahkow S and Moseley S L. Specific DNA Probes in Diagnostic Microbiology.
22. U.S. Pat. No. 4,751,080, issued Jun. 14, 1988, to Wyatt R G, Kapikian A Z, Chanock R M, Midthum K, Flores J, Hoshino Y. Vaccine Against Rotavirus Diseases.
23. U.S. Pat. No. 4,814,268, issued Mar. 21, 1989, to Kreider J W and Howett M. K. Methods for Propagating Fastidious Human Viruses and for Producing Purified Suspensions Thereof.

SUMMARY OF THE INVENTION

It is therefore an object of the invention to characterize the Norwalk and related virus genomes by synthesizing and cloning a cDNA library.

It is an associated object of the invention to deduce amino acid sequences from the cDNA.

Another object of the invention is to develop a method of preparing polyclonal and monoclonal antibodies to the Norwalk and related viruses.

Still another object of the invention is to develop a method of making probes to detect Norwalk and related viruses.

A further object of the invention is to use the cDNA or fragments or derivatives thereof in assays to detect Norwalk and related viruses in samples suspected of containing the viruses.

A still further object of the invention is to express proteins to measure antibody responses.

A nucleotide sequence of the genome sense strand of the Norwalk virus cDNA clone according to the presently preferred embodiment of the invention intended to accomplish the foregoing objects includes the nucleotide sequence shown in Table 1. Within the nucleotide sequence are regions which encode proteins. The nucleotide sequence of the Norwalk virus genome, its fragments and derivatives are used to make diagnostic products and vaccines.

Other and still further objects, features and advantages of the present invention will be apparent from the following description of a presently preferred embodiment of the invention.

BRIEF DESCRIPTION OF THE FIGURES

FIG. 2a. Hybridization of stool samples with $^{32}$P-labeled plasmid DNA for screening positive Norwalk cDNA clones. Nucleic acids from paired stools [before (b) and after (a) infection with Norwalk virus] from two volunteers (1 and 2) were dotted on Zetabind filters. Replicate strips were prepared and hybridized at 50° C. and 65° C. with each test clone (pUC-27, pUC-593, pUC-13 and pUCNV-953). One clone (pUCNV-953) which reacted only with stool samples after (but not before) Norwalk infection was considered as a potential positive clone and was chosen for further characterization.

FIG. 5. The nucleotide sequence of the genome sense strand of the first Norwalk virus cDNA clone. The deduced amino acid sequence of a long open reading frame in this cDNA is also shown.

FIG. 8. Norwalk virus encodes an RNA-directed RNA polymerase sequence motif. The deduced amino acid sequence of a portion of Norwalk virus pUCNV-4095 (NV) is compared with consensus amino acid residues thought to encode putative RNA-directed RNA polymerases of hepatitis E virus (HEV), hepatitis C virus (HCV), hepatitis A virus (HAV), Japanese encephalitis virus (JE), poliovirus (polio), foot-and-mouth disease virus (FMD), encephalomyocarditis virus (EMC), Sindbis virus (SNBV), tobacco mosaic virus (TMV), alfalfa mosaic virus (AMV), brome mosaic virus (BMV), and cowpea mosaic virus (CpMV). Sequences for viruses other than NV are from FIG. 3 of Reyes et al., Science 247:1335–1339.

DETAILED DESCRIPTION OF THE INVENTION

Figure 1:
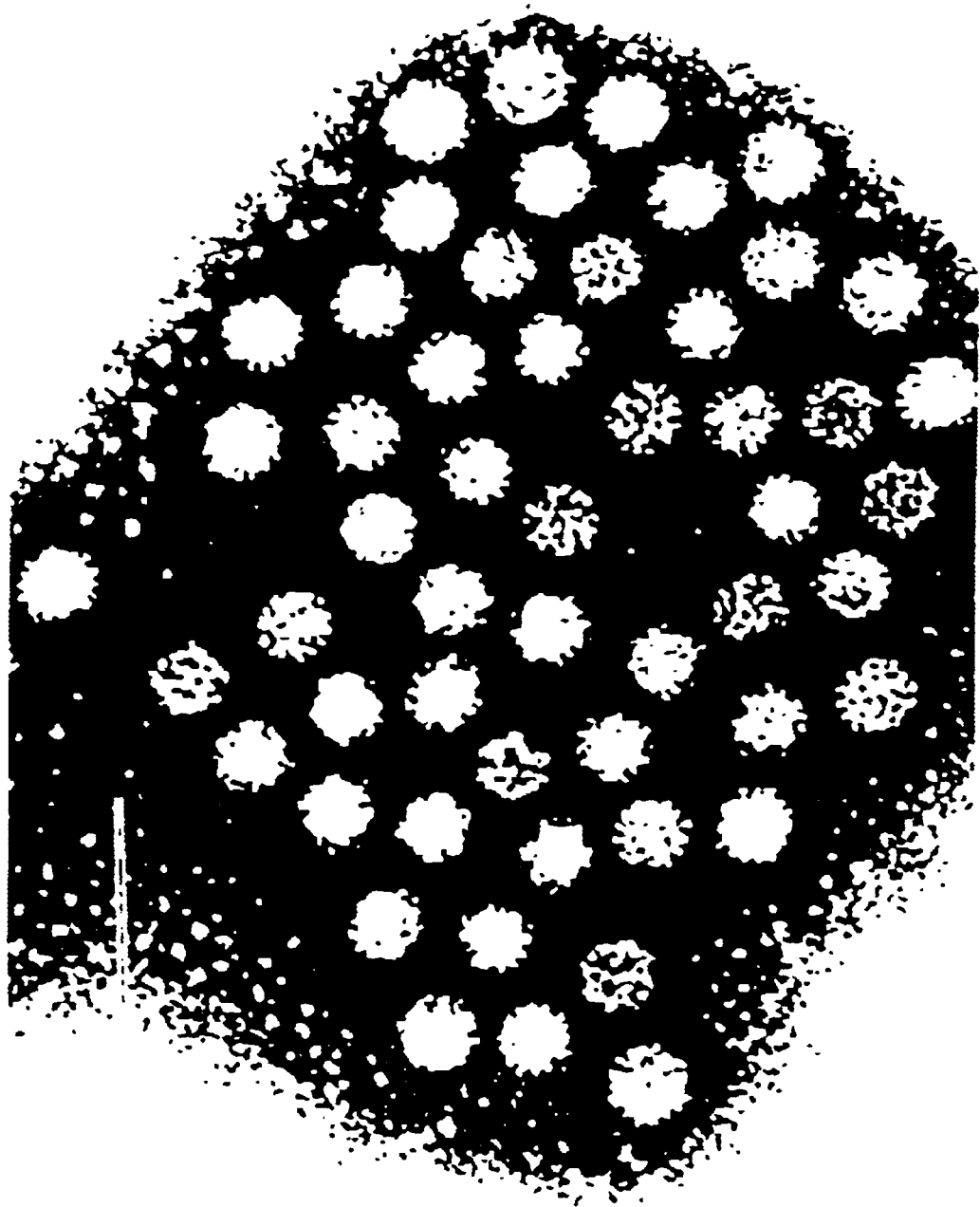
FIG. 1. EM picture of Norwalk viruses after CsCl gradient purification.

It is readily apparent to one skilled in the art that various substitutions and modifications may be made to the invention disclosed herein without departing from the scope and spirit of the invention.

The term "fragment" as used herein is defined as a fragment of a genome or a subgenomic clone that is required to be expressed to produce a peptide fragment which might be able to induce a polyclonal or monoclonal antibody. It is possible a peptide of only 5 amino acids could be immunogenic but usually peptides of 15 amino acids or longer are required. This depends on the properties of the peptide and it cannot be predicted in advance.

The term "derivative" as used herein is defined as larger pieces of DNA or an additional cDNA which represents the Norwalk genome and which is detected by direct or sequential use of the original cDNA and any deduced amino acid sequences thereof. Clone pUCNV-1011, therefore, is a derivative, although it does not overlap or share sequences with the original clone. Also included within the definition of derivative are RNA counterparts of DNA fragments and DNA or cDNA fragments in which one or more bases have been substituted or to which labels and end structures have been added without affecting the reading or expression of the DNA or cDNA.

Production of Norwalk Virus for Molecular Cloning

Norwalk virus was produced by administration of safety tested Norwalk virus (8FIIa) to adult volunteers. The virus inoculum used in the volunteer study, was kindly supplied by Dr. Albert Kapikian (Laboratory of Allergy and Infectious Diseases, National Institutes of Health, Bethesda, Md.). This virus originated from an outbreak of acute gastroenteritis in Norwalk, Ohio (Dolin et al., 1971). Two ml of a 1 to 100 dilution of 8FIIa in TBS was administered orally to each individual with 80 ml of milli-Q water (Millipore, Bedford, Mass. 01730). Sodium bicarbonate solution was taken by each person 2 minutes before and 5 minutes after virus administration. The volunteer studies were approved by the Institutional Review Board for Human Research at Baylor College of Medicine, at the Methodist Hospital and at the General Clinical Research Center. The virus was administered to the volunteers in the General Clinical Research Center where the volunteers were hospitalized and under extensive medical care for 4 days. All stools were collected and kept at −70° C. for later use.

Purification of Norwalk Viruses from Stool Samples

A 10% solution of stool samples in TBS was clarified by low speed centrifugation at 3000 rpm for 15 min. The resultant supernate was then extracted two to three times with genetron in the presence of 0.5% Zwittergent 3-14 detergent (Calbiochem Corp., La Jolla, Calif.). Viruses in the aqueous phase were concentrated by pelleting at 36,000 rpm for 90 minutes through a 40% sucrose cushion in a 50.2 Ti rotor (Beckman Instruments, Inc., Palo Alto, Calif. 94304). The pellets were suspended in TBS and mixed with CsCl solution (refractive index 1.368) and centrifuged at about 35,000 rpm for about 24 h in a SW50.1 rotor (Beckman). The CsCl gradient was fractionated by bottom puncture and each fraction was monitored for virus by EM examination. The peak fractions containing Norwalk virus were pooled and CsCl in the samples was diluted with TBS and removed by pelleting the viruses at about 35,000 rpm for 1 h. The purified virus was stored at about −70° C.

Extraction of Nucleic Acids from Purified Virus

One method of extraction involved treating purified Norwalk virus from CsCl gradients with proteinase K (400 ug/ml) in proteinase K buffer (0.1 M Tris-Cl pH 7.5, 12.5 mM EDTA, 0.15 M NaCl, 1% w/v SDS) at about 37° C. for about 30 min. The samples were then extracted once with phenol-chloroform and once with chloroform. Nucleic acids in the aqueous phase were concentrated by precipitation with 2.5 volumes of ethanol in the presence of 0.2 M NaOAc followed by pelleting for 15 min in a microcentrifuge.

cDNA Synthesis and Cloning of Amplified of cDNA

One method of synthesis and cloning included denaturing nucleic acids extracted from the purified Norwalk viruses with 10 mM $CH_3HgOH$. Then cDNA was synthesized using the cDNA synthesis kit with the supplied random hexanucleotide primer (Amersham, Arlington Heights, Ill. 60005). After the second strand synthesis, the reaction mixture was extracted once with phenol-chloroform and once with chloroform followed by ethanol precipitation. Amplification of DNA was performed using the random prime kit for DNA labeling (Promega Corp., Madison, Wis. 53711-5305). Eight cycles of denaturation (100° C. for 2 min), reannealing (2 min cooling to room temperature) and elongation (room temperature for 30 min) were performed after addition of Klenow fragment (Promega Corp.). A DNA library was constructed in pUC-13 with blunt-end ligation into the Sma I site.

Screening of the Library for Positive Clones

As one method of screening, white colonies from transformed DH5 alpha bacterial cells (BRL) were picked and both a master plate and minipreps of plasmid DNA were prepared for each clone. Clones containing inserts were identified after electrophoresis of the plasmid DNA in an agarose gel. The insert DNA in the agarose gel was cut out and labeled with $^{32}P$ using random primers and Klenow DNA polymerase such as in the prime-a-gene® labeling system (Promega Corp.). Other isotopic or biochemical labels, such as enzymes, and fluorescent, chemiluminescent or bioluminescent substrates can also be used. Nucleic acids extracted from paired stool samples (before and after Norwalk infection) from two volunteers (543 and 544) were dotted onto Zetabind filters (AFM, Cuno, Meriden, Conn.). Replicate filter strips were prepared and hybridized with each labeled plasmid probe individually at 65° C. without formamide. Potential positive clones were judged by their different reactions with the pre- and post-infection stools. Clones which reacted with post (but not pre-) infection stools of volunteers were considered positive and these clones on the master plates were characterized further. Once one Norwalk clone was identified, it was used to rescreen the cDNA library to identify additional overlapping clones. Rescreening the cDNA library with these additional clones can ultimately identify clones representing the entire Norwalk virus genome.

The following examples are offered by way of illustration and are not intended to limit the invention in any manner.

EXAMPLE 1

Electron Micrograph Confirmation

To permit better diagnosis and molecular characterization of Norwalk virus, a cDNA library was derived from nucleic acid extracted from virions purified from stool samples. Norwalk virus was purified with methods used previously for hepatitis A and rotaviruses from stool samples with some modifications (Jiang et al., 1986). Basically stool samples obtained from volunteers administered Norwalk virus were treated with Genetron to remove lipid and water insoluble materials. Virus in the aqueous phase was then pelleted through a 40% sucrose cushion. The resultant pellets were resuspended, sonicated and loaded in a CsCl gradient for isopycnic centrifugation. FIG. 1 shows an electron micrograph of purified Norwalk viruses after CsCl gradient centrifugation. Approximately $10^9$ physical particles were obtained from 500 grams of stools when the first cDNA library was made.

EXAMPLE 2

Initial cDNA Synthesis, Cloning and Screening

A cDNA library was generated from nucleic acids extracted from these purified viruses by proteinase K treatment of the samples followed by phenol-chloroform extraction and ethanol precipitation (Jiang et al., 1986; 1987). Because the nature of the viral genome was unknown, the extracted nucleic acids were denatured with methylmercuric hydroxide before cDNA synthesis. Random primed cDNA was synthesized with the Gubler-Hoffman method (cDNA synthesis system plus, Amersham) and a small amount of cDNA was obtained. Direct cloning of this small amount of cDNA was unsuccessful. Therefore, a step of amplification of the DNA was performed by synthesizing more copies of the DNA with random primers and the Klenow fragment of DNA polymerase before cloning. The procedure involved cycles of denaturation, addition of random primers and the Klenow fragment of DNA polymerase, reannealing and elongation. With this procedure, a linear incorporation of labeled nucleotides into product was observed as the number of cycles of synthesis was increased. The numbers of cycles performed were limited (<10) to avoid the synthesis of an excess of smaller fragments. In the case of Norwalk cDNA, 8 cycles of amplification were performed and approximately 2.5 ug of DNA were obtained, which was at least a 100-fold amplification of the starting template cDNA. This amplified cDNA was cloned into pUC-13 by blunt-end ligation and a positive clone (pUCNV-953) was isolated.

To obtain the positive Norwalk virus clone, minipreparations of the plasmid DNAs containing potential inserts were screened by agarose gel electrophoresis. Inserts of the larger clones in the gel were cut out and probes were made with the DNA in the gel using the prime-a-gene® labeling system (Promega Corp.). These probes were hybridized individually with paired stool samples (before and after Norwalk infection) from two volunteers (FIG. 2a). One clone (pUCNV-953) reacted with post- but not pre-infection stool samples from both volunteers.

EXAMPLE 3

Confirmation of Viral Origin of the Clone pUCNV-953

Figure 2B:
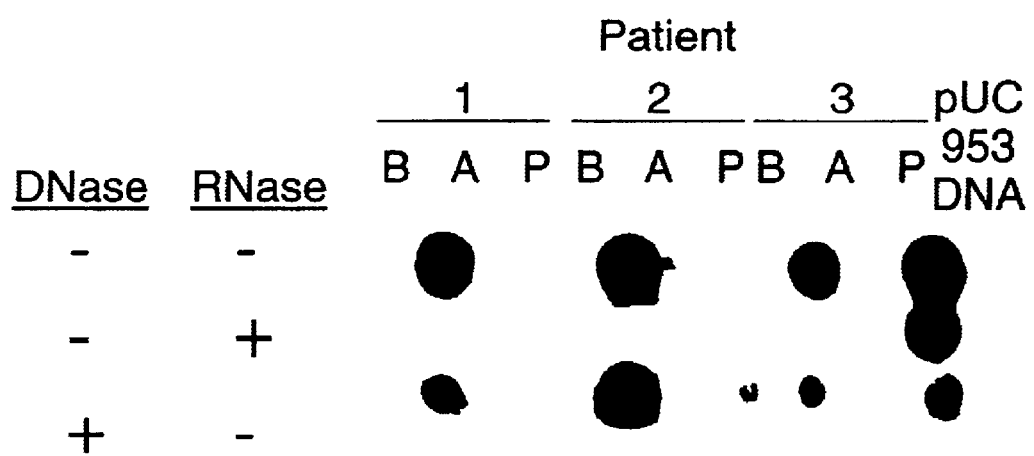
FIG. 2b. Dot blot hybridization of clone $^{32}$P-labeled pUCNV-953 with another 3 sets of stool samples collected at different times after infection (B=before acute phase of illness; A=acute phase of illness; P=post-acute phase of illness) of 3 volunteers. The nucleic acids were dotted directly or after treatment with RNAse or with DNAse before dotting. Double-stranded homologous cDNA (pUCNV-953) was dotted after the same treatments as the stool samples.
Figure 3:
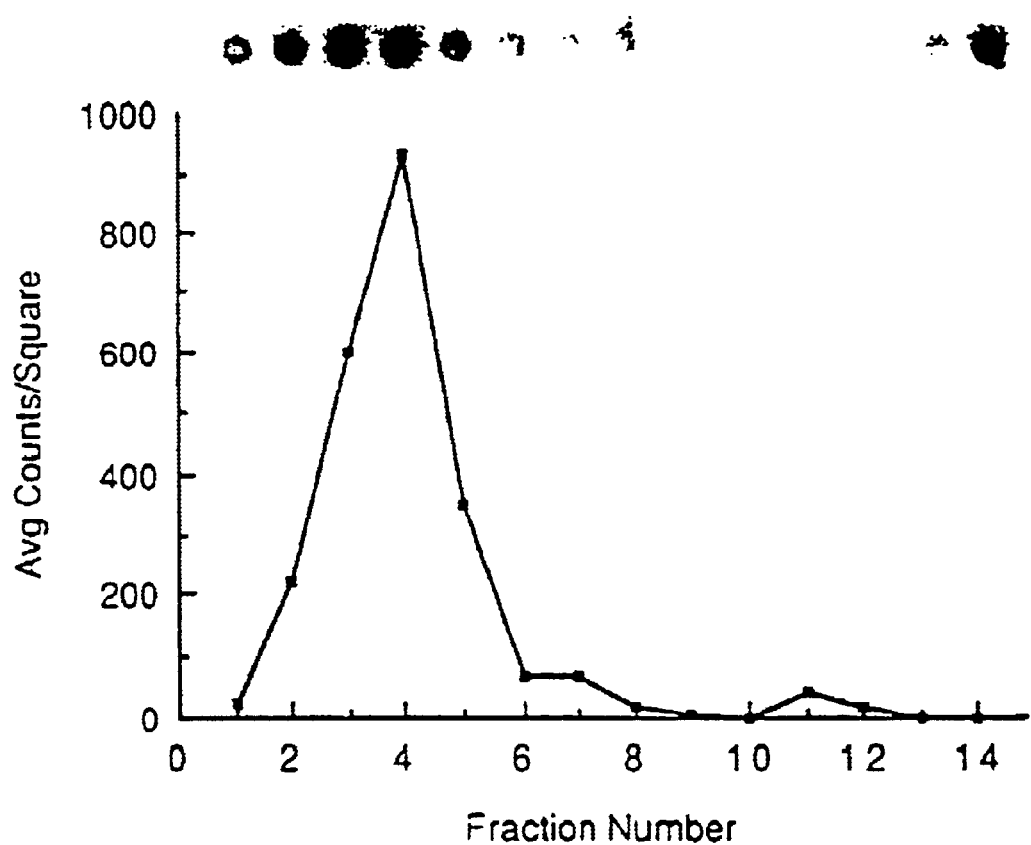
FIG. 3a. Dot blot hybridization of Norwalk viruses in a CsCl gradient with ssRNA probes made from pGEMNV-953. Aliquots of 50 ul from each fraction in a CsCl gradient were dotted onto a Zetabind filter. Duplicates of filters were made and hybridized with the two ssRNA probes respectively. The two strands were subsequently called cRNA (positive hybridization with the viral nucleic acid) and vRNA (no hybridization with the viral nucleic acid, data not shown). The graph shows EM counts of Norwalk viruses from each fraction of the same CsCl gradient for the dot blot hybridization. Five squares from each grid were counted and the average of the number of viral particles per square was calculated.
Figure 4:
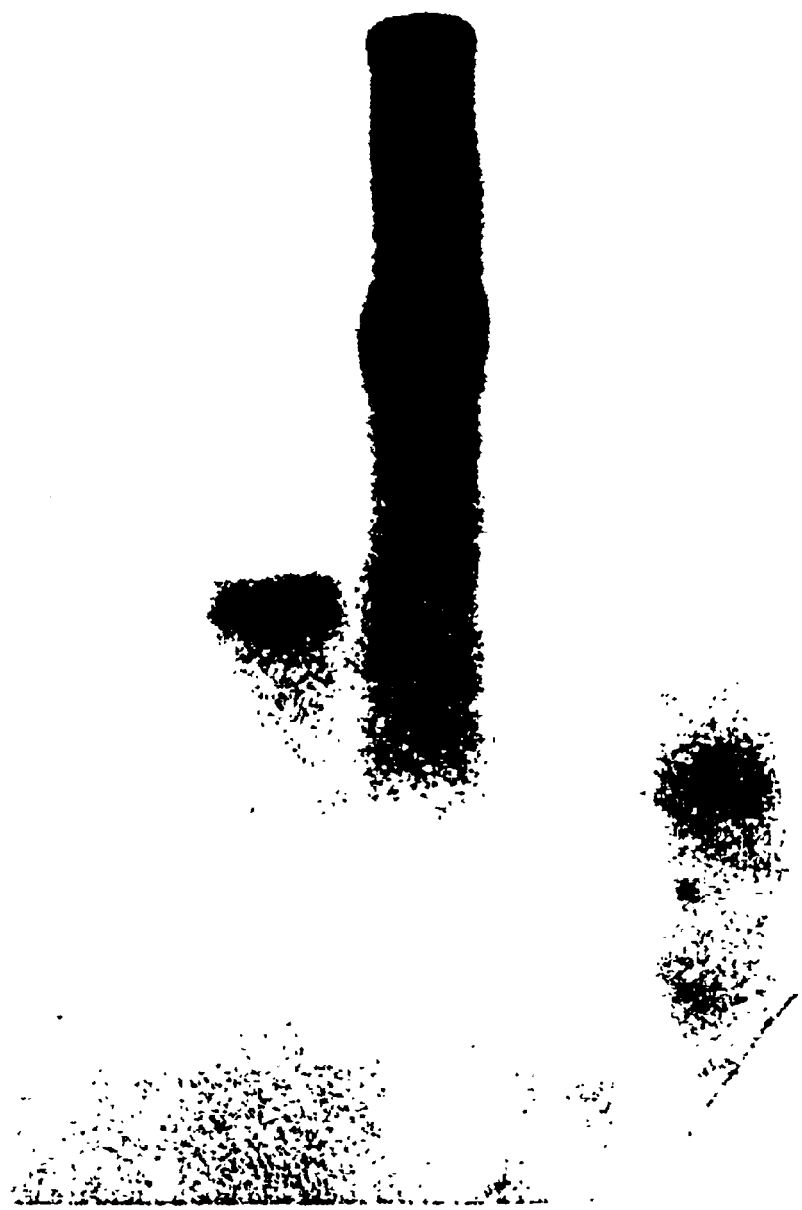
FIG. 4. Hybridization of Norwalk viral RNA with $^{32}$P-labeled clone pUCNV-953. Nucleic acids extracted from partially purified viruses were electrophoresed in a native agarose gel as described previously (Jiang et al., 1989). The gel was then dried at 80° C. for 1 h and hybridized with $^{32}$P-labeled pUCNV-953 insert. Lane 1, 23 S and 16 S rRNA from E. coli (Miles Laboratories Inc., Naperville, Ill. 60566), lanes 2 and 4, total nucleic acids from partially purified stool samples containing Norwalk virus, and lane 3, HAV RNA.

To further confirm the viral origin of the clone pUCNV-953, 6 more paired stool samples were tested and the same results were obtained. FIG. 2b shows a dot blot hybridization of the clone with stool samples collected at different times post-infection of the disease. Strong signals were observed only with stools from acute phase, but not before and after the illness. This result was consistent with previous RIA assays for viral antigen detection using convalescent sera from volunteers with Norwalk diarrhea and immune electron microscopy (IEM) studies of the samples for viral particle examination. This result also agrees with the patterns of virus shedding in stool in the course of the disease (Thornhill et al., 1975). When the clone was hybridized with fractions of a CsCl gradient from the Norwalk virus purification scheme, a correlation between hybridization and EM viral particle counts was observed (FIG. 3). The peaks of the hybridization signals and viral particle counts both were at fractions with a density of 1.38 g/cm$^3$, which agrees with previous reports of the biophysical properties of Norwalk virus. Finally, the clone was tested by hybridization with highly purified Norwalk virus electrophoresed on an agarose gel. A single hybridization band was observed with Norwalk virus but not with HAV (FIG. 4) and rotavirus (not shown). Sequence analysis of the pUCNV-953 cDNA showed this clone is 511 bp (FIG. 5). This partial genomic cDNA encodes a potential open reading frame for which the amino acid sequence has been deduced (FIG. 5). No significant nucleotide or deduced amino acid sequence homology was found by comparison with other sequences in the Gen Bank (Molecular Biology Information Resource, Eugene Software, Baylor College of Medicine).

EXAMPLE 4

Use of Norwalk Virus cDNA to Characterize the Viral Genome

The pUCNV-953 cDNA was subcloned into the transcription vector pGEM-3Zf(+) and grown. ssRNA probes were then generated by in vitro transcription using SP6 and T7 polymerases (Promega). When two opposite sense ssRNA probes were hybridized with the viral nucleic acid separately, only one strand reacted with the virus, indicating the viral genome is single-stranded. As shown in FIG. 2b, the hybridization signals were removed by treatment of the viral nucleic acid with RNAse (but not with DNAse) before loading them onto the filters, indicating the virus genome contains ssRNA. A long open reading frame was found in one of the two strands of the inserted DNA by the computer analysis of the sequences of pUCNV-953. The ssRNA probe with the same sequence as this coding strand does not react with the viral nucleic acid, but the complementary ssRNA probe does react in the hybridization tests. Therefore, Norwalk virus contains a positive sense single-stranded RNA genome. The size of the genome of Norwalk virus was estimated to be about 8 kb based on comparisons of the migration rate of the purified viral RNA in agarose gels with molecular weight markers. This size is slightly bigger than that of the picornaviruses [HAV and poliovirus; (FIG. 4)].

Figure 6:
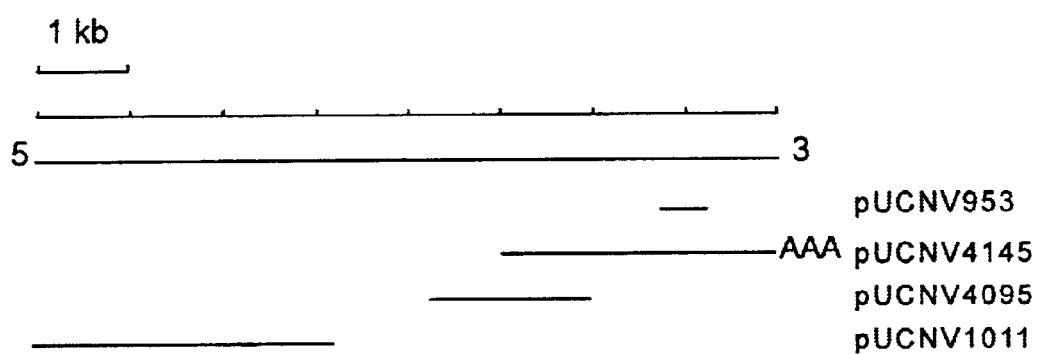
FIG. 6. Physical map of Norwalk virus specific clones isolated from the pUC-13 library. This map assumes the Norwalk genome is 8 kb and shows only a subset (the four largest) of ~100 characterized clones. cDNAs which represent at least 7 kb of nucleic acid have been identified by hybridization with pre- and post infected stool samples, or by rescreening the library with 5'-end probes of the original (pUCNV-953) and subsequent positive clones. A poly(A) tail (~80 bases) is present at the 3'-end of clone pUCNV-4145. Clone pUCNV-1011 also hybridized specifically with post (but not pre-) infection stools from volunteers (see FIG. 7).
Figure 7:
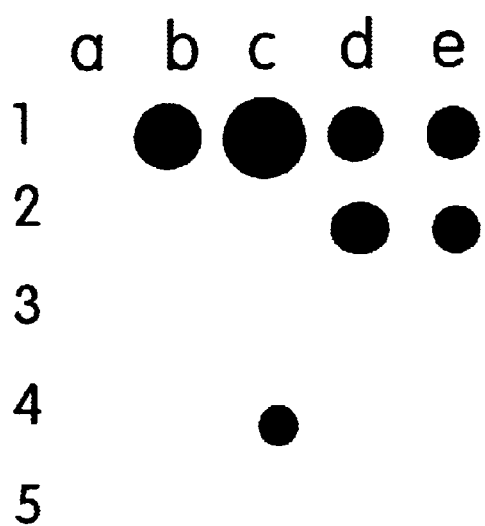
FIG. 7. Dot blot hybridization of stool samples with $^{32}$P-labeled probes representing the 3'- and 5'-end of the Norwalk viral genome. Stool samples were collected from 5 human volunteers at different times (a–e) after infection with Norwalk virus. Samples in column (a) were collected in the first 24 h post-infection, before symptoms appeared. The rest of the stool samples were collected from day 2 to day 5 post-infection. Nucleic acids were extracted and duplicate dots were immobilized on a Zetabind filter. The 3'- and 5'-end probes were derived from clones pUCNV-953 and pUCNV-1011, respectively (see FIG. 6 for description of clones).

The pUCNV-953 cDNA was used to rescreen a second cDNA library made as follows. A clone of the Norwalk or related virus was synthesized by isolating nucleic acid from purified Norwalk virus; cDNA was synthesized using reverse transcriptase and random primers; a second strand of DNA was synthesized from the cDNA; and at least one copy of DNA was inserted into a plasmid or a cloning and expression vector; and screening the library with the original puCNV-953 cDNA identified clones containing fragments of (or the complete) Norwalk or related genome. Alternatively at least one copy of DNA was inserted in a cloning and expression vector, such as lambda ZAPII® (Stratigene Inc.), and the cDNA library was screened to identify recombinant phage containing fragments of or the complete Norwalk or related genome. Additional cDNAs were made and found with this method. Use of these additional cDNAs to rescreen the library resulted in detection of new clones (FIG. 6). Use of the original pUCNV-953 and one additional non-overlapping cDNA (pUCNV-1011) as probes confirmed they detected virus (FIG. 7). Other overlapping cDNA (pUCNV-4145) and non-overlapping cDNA (pUCNV-4095) are useful probes to detect the Norwalk and related viruses.

Thus, the cDNA, or fragments or derivatives thereof, can be used in assays to detect the genome of Norwalk and other related viruses. The detection assays include labeled cDNA or ssRNA probes for direct detection of the Norwalk virus genome and measurement of the amount of probe binding. Alternatively, small oligonucleotide probes (10 nucleotides or greater) and polymerase chain reaction amplification are used to detect the Norwalk and related virus genomes. Expression of the open reading frame in the cDNA is used to make hyperimmune or monoclonal antibodies for use in diagnostic products and vaccines.

Using the above methodology, the nucleotide sequence in Table 1 was identified. Within that nucleotide sequence, the encoding regions for several proteins have been identified. In that sequence, the first protein is encoded by nucleotides 146 through 5339 and the amino acid sequence is shown in Table 2. This first protein is eventually cleaved to make at least three proteins including a picornavirus 2c-like protein, a 3C-like protease and an RNA-dependent RNA polymerase. The fact that this portion of the genome contains an RNA polymerase is verified by comparisons with RNA polymerase in other positive sense RNA viruses (FIG. 8).

Also in the sequence in Table 1, two other protein encoding regions were found. They are encoded by nucleotides 5346 through 6935 and nucleotides 6938 through 7724. The amino acid sequences for these two proteins are shown in Tables 3 and 4, respectively.

EXAMPLE 5

Diagnostic Assays Based on Detection of the Sequences of the Norwalk Virus Genome Hybridization assays are the assays of choice to detect Norwalk virus because small amounts of virus are present in clinical or contaminated water and food specimens. Previously, the possibility to detect Norwalk and related nucleic acids was not possible because the genome of Norwalk virus was not known and no sequence information was available. Probes made from the Norwalk virus cDNA or primers made from the Norwalk virus genome sequence allow methods to amplify the genome for diagnostic products to be established. Probes to identify Norwalk virus alone and to identify other viruses in the Norwalk group enable development of either specific assays for Norwalk or general assays to detect sequences common to many or all of these agents.

In the past, one major difficulty encountered in RT-PCR detection of viral RNA in stool samples was that uncharacterized factor(s) are present in stools which inhibit the enzymatic activity of both reverse transcriptase and Taq polymerase (Wilde et al., J Clin Microbiol 28:1300–1307, 1990). These factor(s) were difficult to remove by routine methods of nucleic acid extraction. Techniques were developed using cetyltrimethylammonium bromide (CTAB) and oligo d(T) cellulose to specifically separate viral RNA from the inhibitory factor(s). These techniques were based on the unique properties of CTAB which selectively precipitates nucleic acid while leaving acid insoluble polysaccharide in the supernatant. The resulting nucleic acid was further purified by adsorption onto and elution from oligo d(T) cellulose. This step removes unrelated nucleic acids that lack a poly(A) tail. With this technique, Norwalk virus was detected easily by PCR in very small amounts (400 ul of a 10% suspension) of stool sample. For example, one skilled in the art will recognize that it is now possible to clone the genome of RNA viruses present in low concentrations in small amounts of stool after RT-PCR and a step of amplification of the viral RNA by RT-PCR using random primers. In some cases, RT-PCR active nucleic acids are extracted with CTAB and without oligo d(T) cellulose. In addition, now that the inhibitor(s) can be removed from stool, it will also be possible to detect and clone nucleic acids of other viruses (DNA viruses, non-poly(A) tailed RNA viruses) present in stool.

The CTAB and oligo d(T) cellulose technique of extraction followed by detection of viral RNA with RT-PCR was used on stool samples and could be used on water and food samples. Stool sample was suspended in distilled water (about 10% wt/vol) and extracted once with genetron. Viruses in the supernatant were precipitated with polyethylene glycol at a final concentration of about 8%. The viral pellets were treated with proteinase K (About 400 ug/ml) in the presence of SDS at about 37° C. for about 30 min. followed by one extraction with phenol chloroform and one with chloroform. A solution of about 5% CTAB and about 0.4M NaCl was added at a ratio of sample:CTAB=about 5:2. After incubation at about room temperature for about 15 min and at about 45° C. for about 5 min, the nucleic acids (including the viral RNA) were collected by centrifugation in a microcentrifuge for about 30 min. The resultant pellets were suspended in about 1M NaCl and extracted twice with chloroform. The viral RNA in the aqueous phase was used directly in RT-PCR reactions or further purified by adsorption/elution on oligo d(T) cellulose.

A batch method of adsorption/elution on oligo d(T) cellulose was used to purify poly(A) tailed RNA. In this procedure, nucleic acids partially purified as described above or RNA extracted directly with phenol chloroform (without CTAB treatment) were mixed with oligo d(T) cellulose (about 2–4 mg/sample) in a binding buffer (about 0.5M NaCl and 10 mM Tris, pH 7.5). The mixture was incubated at about 4° C. for about 1 hr with gentle shaking and then centrifuged for about 2 min in a microcentrifuge. The oligo d(T) cellulose pellet was washed 3–4 times with binding buffer and then the poly(A) tailed RNA was eluted with 1×TE buffer (about 1 mM Tris, 1 mM EDTA, pH 7.5). The supernate was collected following centrifugation to remove the oligo d(T) cellulose and the viral RNA in the supernate was precipitated with ethanol. The RNA obtained at this stage was basically inhibitor-free and able to be used in RT-PCR.

In preliminary experiments, Norwalk virus RNA was detected in less than 0.05 g of stool samples using the CTAB technique. A trace inhibitor activity was observed with RNA extracted with either CTAB or oligo d(T) alone, but this was easily removed by dilution (1:2) of the extracted nucleic acid before RT-PCR. Combination of the CTAB and oligo d(T) techniques resulted in obtaining high quality, inhibitor free RNA which could be used directly for RT-PCR detection and for cloning of the viral genome. With development of this method to clone from small amounts of stool, one skilled in the art will know that we will now be able to obtain cDNAs for the remainder of the genome including those representing the 5'-end of the genome.

Figure 9:
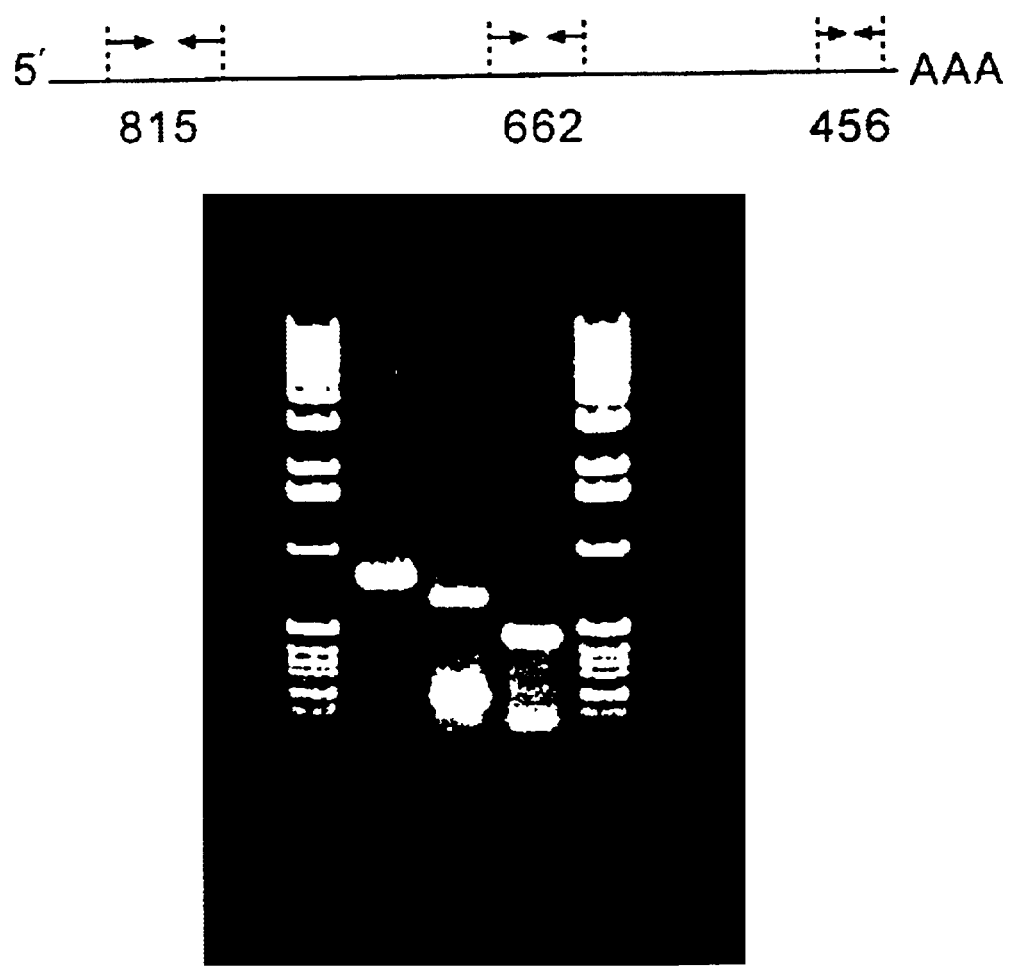
FIG. 9. Three sets of primers used to amplify the Norwalk virus genome.

For detection with PCR, primers based on the above nucleotide sequence of the genome were made by chemical methods. These primers include: Primer 1: CACGCGGAG-GCTCTCAAT located at nucleotides 7448 to 7465; Primer 4: GGTGGCGAAGCGGCCCTC located at nucleotides 7010 to 7027; Primer 8: TCAGCAGTTATAGATATG located at nucleotides 1409 to 1426; Primer 9: ATGC-TATATACATAGGTC located at nucleotides 612 to 629; Primer 16: CAACAGGTACTACGTGAC located at nucleotides 4010 to 4027; and Primer 17: TGTGGCCCAA-GATTTGCT located at nucleotides 4654 to 4671. These primers have been shown to be useful to detect virus using reverse transcription and polymerase chain reaction methods (RT-PCR). FIG. 9 shows data using these primers. In primer sets 1 and 4, 8 and 9, and 16 and 17, the reverse compliments for the sequences given above for primers 1, 8, and 17 were used.

EXAMPLE 6

Preparation of Polyclonal Antibodies and Monoclonal Antibodies to Norwalk Virus Proteins Protein(s) encoded in the cDNA fragments or derivatives thereof, is produced in a prokaryotic or eukaryotic expression system and used to immunize animals to produce polyclonal antibodies for diagnostic assays. Prokaryotic hosts may include Gram negative as well as Gram positive bacteria, such as *E. coli, S. tymphimurium, Serratia marcescens,* and *Bacillus subtilis.* Eukaryotic hosts may include yeast, insect or mammalian cells. Immunized animals may include mammals such as guinea pigs, mice, rabbits, cows, goats or horses or other non-mammalian or non-murine species such as chickens. Repeated immunization of these animals with the expressed protein mixed with an adjuvant such as Freund adjuvant to enhance stimulation of an immune response produces antibodies to the protein.

Alternatively, synthetic peptides of greater than 15 amino acids made to match the amino acid sequence deduced from the partial cDNA sequence (or from other sequences determined by sequencing additional cDNAs detected with the original or other clones) are linked to a carrier protein such as bovine serum albumin or lysozyme or cross-linked with treatment with gluteraldehyde and used to immunize animals to produce polyclonal antibodies for diagnostic tests.

The serum of animals immunized with either the expressed protein or with synthetic peptides are tested by immunologic assays such as immune electron microscopy, Western blots (immunoblots) and blocking ELISAs to demonstrate that antibodies to Norwalk and related viruses have been made. Reactivities with the expressed protein or synthetic peptides show specificity of the polyclonal sera. Reactivities with other viruses in the Norwalk group (Snow Mountain Agent, Hawaii Agent, Taunton Agent, etc.) indicate production of a reagent which recognizes cross-reacting epitopes.

Balb\c mice injected with the immunogens as described above and shown to have produced polyclonal antibodies are boosted with immunogen and then sacrificed. Their spleens are removed for fusion of splenocytes with myeloma cells to produce hybridomas. Hybridomas resulting from this fusion are screened for their reactivity with the expressed protein, the peptide and virus particles to select cells producing monoclonal antibodies to Norwalk virus. Screening of such hybridomas with Norwalk-related viruses permits identification of hybridomas secreting monoclonal antibodies to these viruses as well.

The novel features characteristic of this invention are set forth in the appended claims. The present invention is well adapted to carry out the objects and obtain the ends and advantages mentioned, as well as others inherent therein. While presently preferred embodiments of the invention have been described for the purpose of disclosure, numerous changes in the details of synthesis and use described herein will be apparent to those skilled in the art. It should be understood, however, that there is no intention to limit the invention to the specific form disclosed, but on the contrary, the intention is to cover all modifications, alternative means of synthesis and use and equivalents falling within the spirit and scope of the invention.

Development of Diagnostic Assays

Figure 10:
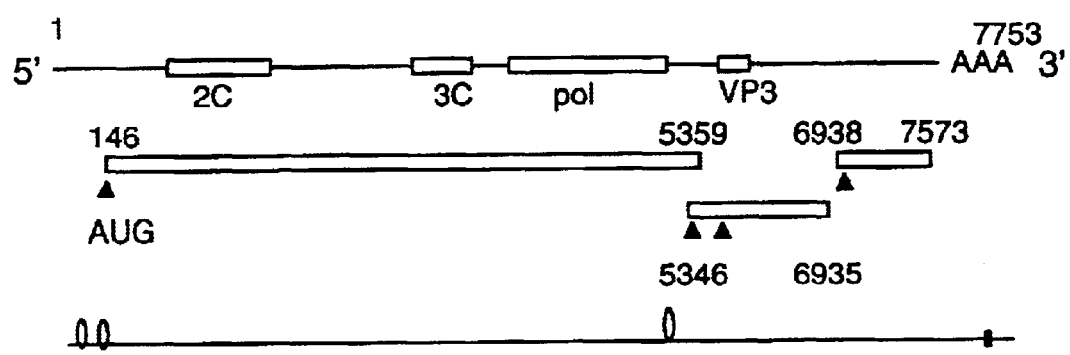
FIG. 10. This schematic shows the organization of Norwalk genome shown in Table 1. The features shown here are based on analyses of the nucleotide sequence of the Norwalk virus genome and the deduced amino acid sequence of proteins encoded in the genome. The genome contains 7753 nucleotides including A's at the 3'-end. Translation of the sequence predicts that the genome encodes three open reading frames (shown by the open boxes). The first open reading frame is predicted to start from an initiation codon at nucleotide 146 and it extends to nucleotide 5359 (excluding the termination codon). The second open reading frame is initiated at nucleotide 5346 and it extends to nucleotide 6935, and a third open reading frame exists between nucleotides 6938 and 7724. Based on comparisons of these predicted proteins with other proteins in the protein databank, the first open reading frame is a protein that is eventually cleaved to make at least three proteins. These three proteins include a picornavirus 2C-like protein, a 3C-like protease and an RNA-dependent RNA polymerase. The second frame encodes the capsid protein.

Analysis of the deduced amino acid sequence of the Norwalk virus genome has shown that the Norwalk virus has the genetic organization shown in FIG. 10. Expression of regions of this genome in cell-free translation systems and in the baculovirus expression system have shown that the 5'-end of the genome encodes nonstructural proteins and the 3'-end of the genome encodes at least one structural protein. Based on this information, one can express the complete genome or subgenomic regions of the genome to produce diagnostic assays to detect viral antigens or immune responses to specific regions of the genome. This information can be used to detect the Norwalk virus, antigens or immune responses to Norwalk virus. This information also can be used to detect other similar currently uncharacterized viruses that cause gastroenteritis or possibly other diseases. Some of these viruses will be in the Caliciviridae or in the picornavirus superfamily. All of these viruses will have matching or similar genomic regions in their DNA sequences. Examples of the diagnostic assays are shown in the specific examples and figures below.

EXAMPLE 7

Development of Diagnostic Assays to Detect Nucleic Acids of Norwalk Virus or Similar Viruses by Detection of Specific Regions of the Viral Genomes Based on an Understanding of the Norwalk Genome The genetic organization of the Norwalk virus genome allows the prediction of specific regions of the gene sequence as regions where oligonucleotide primers or probes can be developed to detect Norwalk virus sequences and common sequences of other related or similar viruses. Some of these common genome sequences will be found in viruses in the Caliciviridae or in the picornavirus superfamily. The detection can be done by standard PCR, hybridization or other gene amplification methods.

EXAMPLE 8

Figure 11:
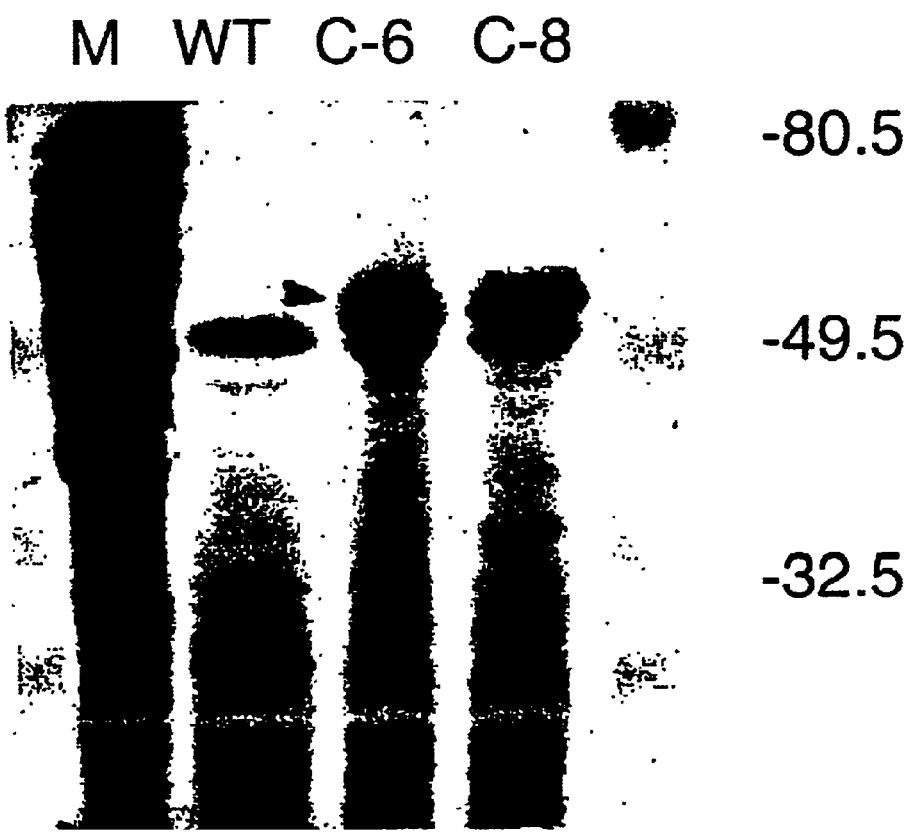
FIG. 11. Expression of the Norwalk virus capsid protein. Baculovirus recombinants (C-6 and C-8) that contain a subgenomic piece of Norwalk virus DNA (from nucleotides 5337 to 7724) were selected and used to infect insect (*Spodoptera fugiperda*) cells at a multiplicity of infection of 10 PFU/cell. After 4 days of incubation at 27° C., the infected cells were harvested and the proteins were analyzed by electrophoresis on 12% polyacrylamide gels. The proteins were visualized after staining with Coomassie blue. The Norwalk-expressed protein (highlighted by the arrow) is only seen in the recombinant-infected cells, but no in wild-type baculovirus (wt) or mock-infected insect cells.

Development of Diagnostic Assay Using Expressed Norwalk Virus Proteins to Detect Immune Response to Norwalk Virus Protein(s) encoded in the Norwalk virus genome or fragments or derivatives thereof is produced in a prokaryotic or eukaryotic expression system and used as antigens in diagnostic assays to detect immune responses following virus infections. Prokaryotic hosts may include Gram negative as well as Gram positive bacteria, such as *Escherichia coli, Salmonella tymphimurium, Serratia marcescens, Bacillus subtilis, Staphylococcus aureus* and *Streptococcus sanguinis*. Eukaryotic hosts may include yeast, insect or mammalian cells. Diagnostic assays may include many format such as enzyme-linked immunosorbent assays, radioimmunoassays, immunoblots or other assays. FIG. 11 shows data for a capsid protein encoded from the 3'-end of the Norwalk virus genome. It is expressed by nucleotides 5337 through 7753 of the DNA sequence shown in Table 1 and FIG. 10. This protein has an approximate molecular weight of 58,500 and is hereinafter referred to as the 58,500 mwt protein. It was produced in insect cells infected with baculovirus recombinants (C-6 and C-8). A band (see arrow in FIG. 11) representing the 58,500 mwt protein in C-6 and C-8 infected cells is not seen in insect cells infected with wild-type (WT) baculovirus or in mock infected cells. Other proteins encoded by Norwalk virus cDNA or fragments or derivatives are similarly expressed using baculovirus recombinants and other expression systems.

Figure 12:
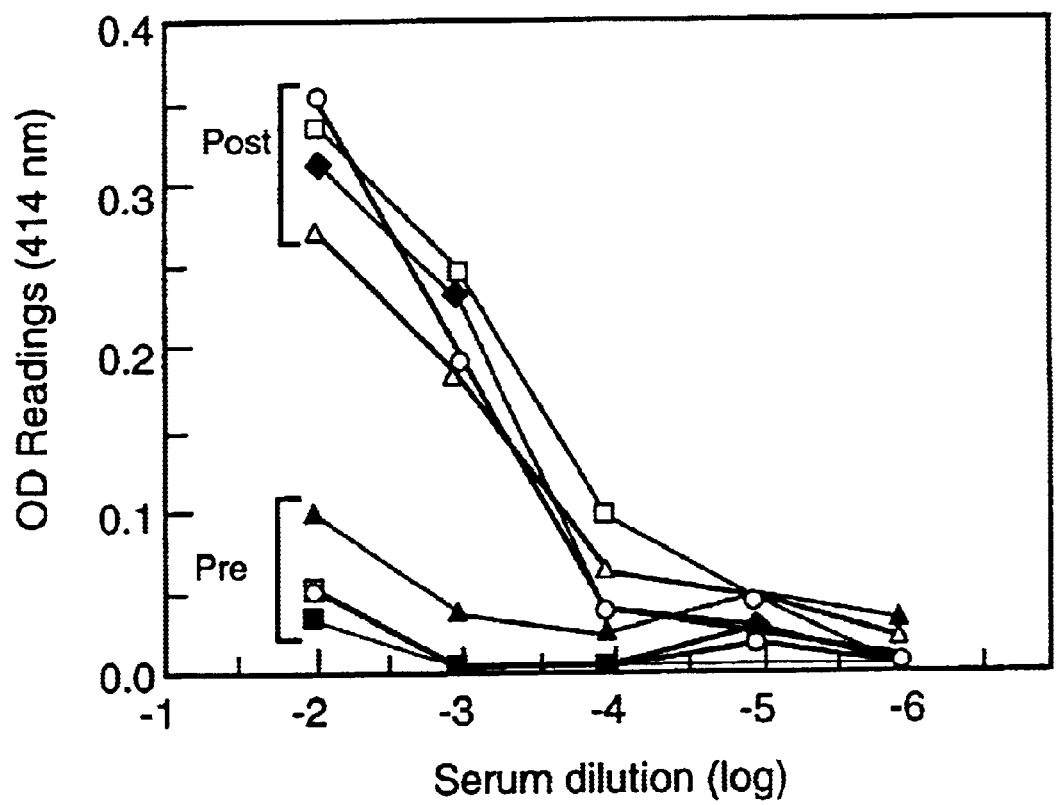
FIG. 12. The Norwalk virus expressed protein shows immunoreactivity with sera from volunteers infected with Norwalk virus. The expressed protein shown in FIG. 11 was absorbed onto the wells of a 96-well ELISA plate and its reactivity was tested with dilutions of serum samples taken from volunteers before (pre) and three weeks after (post) infection with Norwalk virus. After an incubation at 37° C. for 2 hours, a peroxidase-conjugated goat-anti-human IgG, IgM and IgA serum was added and reactivity was subsequently observed by reading the optical density at 414 nm after addition of the substrate. The data show that post-infection sera reacted strongly with the expressed antigen at serum dilutions of 1:100 and 1:1000, and some sera were still reactive at a dilution of 1:1000.

FIG. 12 shows data using the 58,500 mwt protein produced using the baculovirus expression system to detect immune responses before and after infection of volunteers with Norwalk virus inoculum. Antigen was put on ELISA plates and pre- and post-infection human serum was added. The data show that when an individual has had the infection, the post-serum reacts strongly to the antigen. Other proteins encoded in the Norwalk virus cDNA or fragments or derivatives thereof are similarly used to detect immune responses following Norwalk virus infection.

Figure 13:
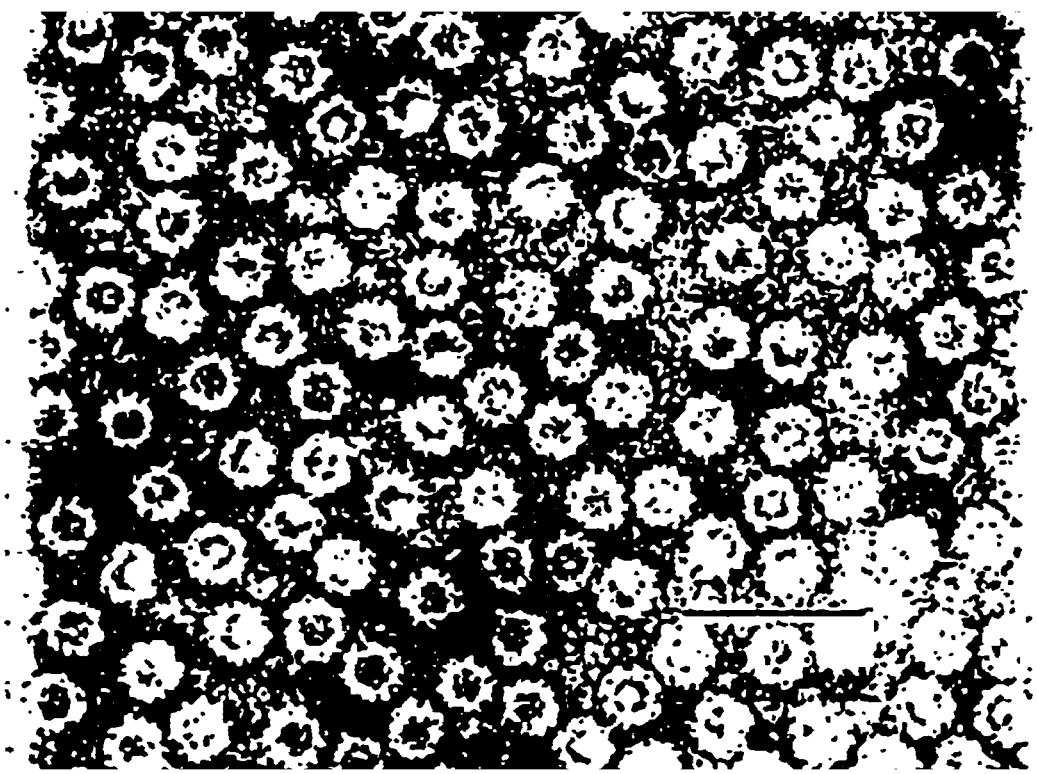
FIG. 13. Baculovirus recombinants containing the 3'-end of the Norwalk genome produce virus-like particles in insect cells. Lysates from insect cells infected with baculovirus recombinant C-8 were analyzed by electron microscopy and shown to contain numerous virus-like particles. These particles are the same size as virus particles obtained from the stools of volunteers infected with Norwalk virus. Bar=50 nm.

Some proteins have the intrinsic property of being able to form particles. The 58,500 mwt protein discussed above has that property. Particles formed from proteins are expressed in any expression system and used to produce diagnostic assays based on detection of antibody responses or immune responses. FIG. 13 shows an electron micrograph of particles produced using the baculovirus expression system from recombinants containing the 3'-end of the Norwalk genome. These particles are similar in size to the native virus particles. They are antigenic, immunoreactive and immunogenic. They differ from most of the virus particles resulting from natural infection in that many of the expressed particles lack nucleic acids.

Figure 14:
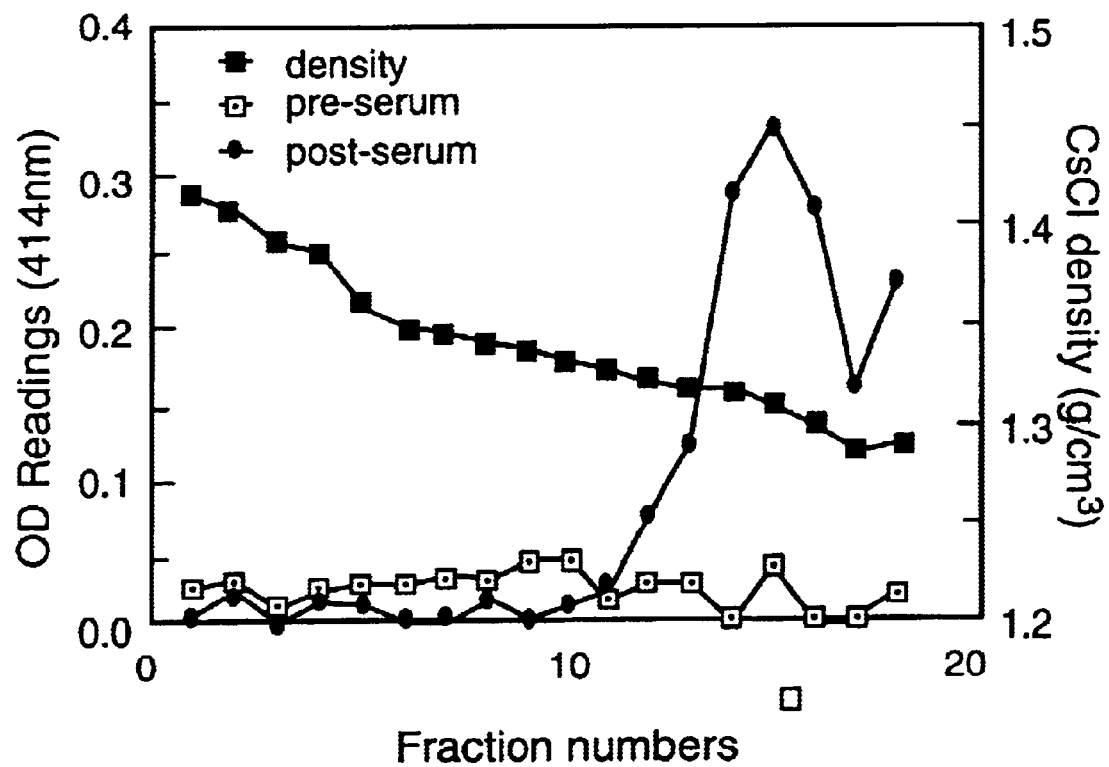
FIG. 14. Norwalk virus-like particles can be purified in gradients of CsCl. Supernatants of insect cells infected with the baculovirus recombinant C-8 were processed by extraction with genetron and PEG precipitation and virus eluted from these PEG pellets was centrifuged in CsCl gradient in a SW50.1 rotor for 24 hours at 4° C. The gradient was fractionated and material in each fraction was adsorbed onto two wells of an ELISA plate. Duplicate wells were then treated either with pre- or post-infection serum, peroxidase-conjugated goat anti-human serum and substrate and the reactions were monitored by reading the OD414 nm. A peak was observed in the gradient at a density of 1.31 g/cm$^3$ and this peak was shown to contain virus-like particles by electron microscopy. This peak also contained a major protein of an approximate molecular weight of 58,500 that comigrated with the protein expressed in the insect cells from the same baculovirus recombinant.

FIG. 14 shows data on the properties of such particles following centrifugation in gradients of CsCl. The density of the particles (symbolized by closed boxes) is 1.31 g/cc which is distinct from the 1.39 g/cc density of particles purified from the original infectious Norwalk inoculum given to volunteers. The gradients were fractionated. Each fraction was put on an ELISA plate and human serum was then introduced. The open boxes show that there was no ELISA activity with the pre-infection serum. The closed diamonds show there was reactivity with the post-infection serum. Other particles made from other proteins encoded in the Norwalk virus cDNA or fragments or derivatives thereof are similarly used to detect immune responses following Norwalk virus infection.

Figure 15:
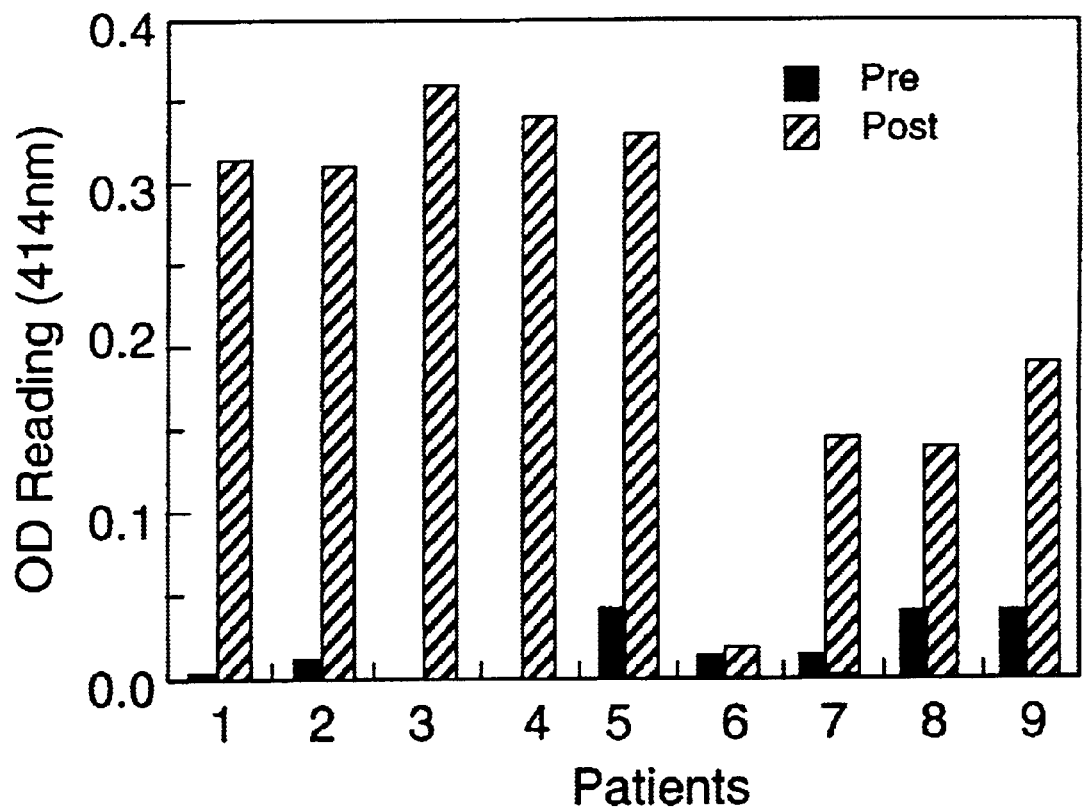
FIG. 15. Use of the expressed virus-like particles to measure the reactivity of pre- and post-serum samples from volunteers infected with Norwalk virus shows that most volunteers have an immune response. Volunteer 6 who did not show an immune response also did not become ill after being administered virus.

FIG. 15 shows data using purified particles formed by the 58,500 mwt protein to detect immune responses in post-inoculation (but not pre-inoculation) serum samples of 9 volunteers infected with Norwalk virus. One of the volunteers, number 6, exhibited no symptoms of Norwalk virus infection based on monitoring clinical symptoms or measuring an immune response. Purified, expressed particles were put on ELISA plates and one pre- and one post-infection serum samples from each volunteer was added to the particles. The amount of antibody binding to the particles in each pre- and post-infection sample was measured. The data in FIG. 15 show that the expressed proteins form particles that are immunoreactive and antigenic. Other proteins encoded in the Norwalk virus cDNA or fragments or derivatives thereof are similarly used to detect immunoreactive and antigenic activity.

EXAMPLE 9

Development of Diagnostic Assays Using Expressed Norwalk Virus Expressed Antigens Individual proteins, particles or protein aggregates formed from expression of one or more Norwalk virus genes in any prokaryotic or eukaryotic expression system are used as an immunogen or inoculate animals to produce polyclonal and monoclonal antibodies for diagnostic assays as previously described above in example 6.

Development of a Vaccine Using Norwalk Virus Expressed Antigens

EXAMPLE 10

Vaccines for Norwalk virus, the Norwalk group of viruses or other small round viruses are made from an expressed Norwalk virus protein. That expressed protein could be a Norwalk virus capsid protein expressed alone or in combination with one or more other Norwalk virus proteins or self-forming particles. For example, the particles shown in FIG. 12 were produced using the baculovirus expression system. They are used as a vaccine when expressed alone or in combination with one or more other Norwalk virus proteins. Similarly, the other proteins encoded in the Norwalk virus cDNA or fragments or derivatives thereof are used as a vaccine when expressed alone or in combination with one or more Norwalk virus proteins.

Individuals are vaccinated orally, parenterally or by a combination of both methods. For parenteral vaccination, the expressed protein is mixed with an adjuvant and administered in one or more doses in amounts and at intervals that give maximum immune response and protective immunity. Oral vaccination parallels natural infection by Norwalk virus inoculum, i.e. the individual ingests the vaccine with dechlorinated water or buffer. Oral vaccination may follow sodium bicarbonate treatment to neutralize stomach activity. For example, sodium bicarbonate solution is taken by each person 2 minutes before and 5 minutes after vaccine administration.

EXAMPLE 11

Production of a Vaccine for other Agents by Using Expressed Norwalk Virus Capsids as a Carrier or Vehicle for the Expression of other Antigens or Parts of other Antigens Identification of the region of the genome that encodes the Norwalk virus capsid protein and that forms particles following expression (i.e., regions 5346 through 6935 and 5337 through 7724) allows genetic engineering of the cDNA that encodes the capsid protein to incorporate one or more heterologous pieces of cDNA that encode antigenic epitopes. Expression of such recombinant genes produces a recombinant capsid that is antigenic, induces antibodies, and protects against Norwalk virus and its antigens, and against the heterologous epitopes or antigens.

Alternatively, the Norwalk virus capsid protein carrier is mixed with or covalently linked to one or more heterologous protein antigens or synthetic peptides containing heterologous epitopes. This mixture and covalent linkage are antigenic, induce antibodies, and protect against Norwalk virus and its antigens, and against the heterologous epitopes or antigens.

Individuals are vaccinated using the oral and parenteral methods described above in example 10.

EXAMPLE 12

Kit

Kits for detecting immune responses to Norwalk virus are prepared by supplying in a container a protein deduced from the Norwalk virus genome shown in Table 1 or fragments or derivatives thereof and produced in an expression system. For example, the protein deduced from nucleotides 1 through 7724 the protein deduced from nucleotides 146 through 5359, the protein deduced from nucleotides 5337 through 7524, the protein deduced from nucleotides 5346 through 6935, the protein deduced from nucleotides 6938 through 7724 and any combinations thereof may be used in such kits. The kit can also include controls for false positive and false negatives, reagents and sample collection devices. The kit can be equipped to detect one sample or multiple samples.

TABLE 1

The nucleotide sequence of Norwalk virus genome.

| | | | | | |
|---|---|---|---|---|---|
| GGCGTCAAAA | GACGTCGTTC | CTACTGCTGC | TAGCAGTGAA | AATGCTAACA | ACAATAGTAG | 60 |
| TATTAAGTCT | CGTCTATTGG | CGAGACTCAA | GGGTTCAGGT | GGGGCTACGT | CCCCACCCAA | 120 |
| CTCGATAAAG | ATAACCAACC | AAGATATGGC | TCTGGGGCTG | ATTGGACAGG | TCCCAGCGCC | 180 |
| AAAGGCCACA | TCCGTCGATG | TCCCTAAACA | ACAGAGGGAT | AGACCACCAC | GGACTGTTGC | 240 |

TABLE 1-continued

The nucleotide sequence of Norwalk virus genome.

```
CGAAGTTCAA CAAAATTTGC GTTGCACTGA GAGACCACAA GACCAGAATG TTAAGACGTG  300

GGATGAGCTT GACCACACAA CAAAACAACA GATACTTGAT GAACACGCTG AGTGGTTTGA  360

TGCCGGTGGC TTAGGTCCAA GTACACTACC CACTAGTCAT GAACGGTACA CACATGAGAA  420

TGATGAAGGC CACCAGGTAA AGTGGTCGGC TAGGGAAGGT GTAGACCTTG GCATATCCGG  480

GCTCACGACG GTGTCTGGGC CTGAGTGGAA TATGTGCCCG CTACCACCAG TTGACCAAAG  540

GAGCACGACA CCTGCAACTG AGCCCACAAT TGGTGACATG ATCGAATTCT ATGAAGGGCA  600

CATCTATCAT TATGCTATAT ACATAGGTCA AGGCAAGACG GTGGGTGTAC ACTCCCCTCA  660

AGCAGCCTTC TCAATAACGA GGATCACCAT ACAGCCCATA TCAGCTTGGT GGCGAGTCTG  720

TTATGTCCCA CAACCAAAAC AGAGGCTCAC ATACGACCAA CTCAAAGAAT TAGAAAATGA  780

ACCATGGCCG TATGCCGCAG TCACGAACAA CTGCTTCGAA TTTTGTTGCC AGGTCATGTG  840

CTTGGAAGAT ACTTGGTTGC AAAGGAAGCT CATCTCCTCT GGCCGGTTTT ACCACCCGAC  900

CCAAGATTGG TCCCGAGACA CTCCAGAATT CCAACAAGAC AGCAAGTTAG AGATGGTTAG  960

GGATGCAGTG CTAGCCGCTA TAAATGGGTT GGTGTCGCGG CCATTTAAAG ATCTTCTGGG  1020

TAAGCTCAAA CCCTTGAACG TGCTTAACTT ACTTTCAAAC TGTGATTGGA CGTTCATGGG  1080

GGTCGTGGAG ATGGTGGTCC TCCTTTTAGA ACTCTTTGGA ATCTTTTGGA ACCCACCTGA  1140

TGTTTCCAAC TTTATAGCTT CACTCCTGCC AGATTTCCAT CTACAGGGCC CCGAGGACCT  1200

TGCCAGGGAT CTCGTGCCAA TAGTATTGGG GGGGATCGGC TTAGCCATAG GATTCACCAG  1260

AGACAAGGTA AGTAAGATGA TGAAGAATGC TGTTGATGGA CTTCGTGCGG CAACCCAGCT  1320

CGGTCAATAT GGCCTAGAAA TATTCTCATT ACTAAAGAAG TACTTCTTCG GTGGTGATCA  1380

AACAGAGAAA ACCCTAAAAG ATATTGAGTC AGCAGTTATA GATATGGAAG TACTATCATC  1440

TACATCAGTG ACTCAGCTGG TGAGGGACAA ACAGTCTGCA GGGGCTTATA TGGCCATCTT  1500

AGATAATGAA GAAGAAAAGG CAAGGAAATT ATCTGTCAGG AATGCCGACC CACACGTAGT  1560

ATCCTCTACC AATGCTCTCA TATCCCGGAT CTCAATGGCT AGGGCTGCAT GGCCAAGGC  1620

TCAAGCTGAA ATGACCAGCA GGATGGGTCC TGTGGTCATT ATGATGTGTG GGCCCCCTGG  1680

TATAGGTAAA ACCAAGGCAG CAGAACATCT GGCTAAAGGC CTAGCCAATG AGATACGGCC  1740

TGGTGGTAAG GTTGGGCTGG TCCCACGGGA GGCAGTGGAT CATTGGGATG GATATCACGG  1800

AGAGGAAGTG ATGCTGTGGG ACGACTATGG AATGACAAAG ATACAGGAAG ACTGTAATAA  1860

ACTGCAAGCC ATAGCCGACT CAGCCCCCCT AACAGTCAAT TGTGACCGAA TAGAAAACAA  1920

GGGAATGCAA TTTGTGTCTG ATGCTATAGT CATCACCACC AATGCTCCTG GCCCAGCCCC  1980

AGTGGACTTT GTCAACCTGG GGCCTGTTTG CCGAAGGGTG GACTTGCTTG TGTATTGCAC  2040

GGCACCTGAA GTTGAACACA CGAGGAAAGT CAGTCCTGGG GACACAACTG CACTGAAAGA  2100

CTGCTTCAAG CCCGATTTCT CACATCTAAA AATGGAGTTG GCTCCCCAAG GGGGCTTTGA  2160

TAACCAAGGG AATACCCGGT TTGGTAAGGG TGTGATGAAG CCCACCACCA TAAACAGGCT  2220

GTTAATCCAG GCTGTAGCCT TGACGATGGA GAGACAGGAT GAGTTCCAAC TCCAGGGGCC  2280

TACGTATGAC TTTGATACTG ACAGAGTAGC TGCGTTCACG AGGATGCCCC GAGCCAACGG  2340

GTTGGGTCTC ATATCCATGG CCTCCCTAGG CAAAAGCTA CGCAGTGTCA CCACTATTGA  2400

AGGATTAAAG AATGCTCTAT CAGGCTATAA AATATCAAAA TGCAGTATAC AATGGCAGTC  2460

AAGGGTGTAC ATTATAGAAT CAGATGGTGC CAGTGTACAA ATCAAAGAAG ACAAGCAAGC  2520

TTTGACCCCT CTGCAGCAGA CAATTAACAC GGCCTCACTT GCCATCACTC GACTCAAAGC  2580
```

TABLE 1-continued

The nucleotide sequence of Norwalk virus genome.

| | | | | | |
|---|---|---|---|---|---|
| AGCTAGGGCT | GTGGCATACG | CTTCATGTTT | CCAGTCCGCC | ATAACTACCA | TACTACAAAT 2640 |
| GGCGGGATCT | GCGCTCGTTA | TTAATCGAGC | GGTCAAGCGT | ATGTTTGGTA | CCCGTACAGC 2700 |
| AGCCATGGCA | TTAGAAGGAC | CTGGGAAAGA | ACATAATTGC | AGGGTCCATA | AGGCTAAGGA 2760 |
| AGCTGGAAAG | GGGCCCATAG | GTCATGATGA | CATGGTAGAA | AGGTTTGGCC | TATGTGAAAC 2820 |
| TGAAGAGGAG | GAGAGTGAGG | ACCAAATTCA | AATGGTACCA | AGTGATGCCG | TCCCAGAAGG 2880 |
| AAAGAACAAA | GGCAAGACCA | AAAAGGGACG | TGGTCGCAAA | AATAACTATA | ATGCATTCTC 2940 |
| TCGCCGTGGT | CTGAGTGATG | AAGAATATGA | AGAGTACAAA | AAGATCAGAG | AAGAAAAGAA 3000 |
| TGGCAATTAT | AGTATACAAG | AATACTTGGA | GGACCGCCAA | CGATATGAGG | AAGAATTAGC 3060 |
| AGAGGTACAG | GCAGGTGGTG | ATGGTGGCAT | AGGAGAAACT | GAAATGGAAA | TCCGTCACAG 3120 |
| GGTCTTCTAT | AAATCCAAGA | GTAAGAAACA | CCAACAAGAG | CAACGGCGAC | AACTTGGTCT 3180 |
| AGTGACTGGA | TCAGACATCA | GAAAACGTAA | GCCCATTGAC | TGGACCCCGC | AAAGAATGA 3240 |
| ATGGGCAGAT | GATGACAGAG | AGGTGGATTA | TAATGAAAAG | ATCAATTTTG | AAGCTCCCCC 3300 |
| GACACTATGG | AGCCGAGTCA | CAAAGTTTGG | ATCAGGATGG | GGCTTTTGGG | TCAGCCGGAC 3360 |
| AGTGTTCATC | ACAACCACAC | ATGTAGTGCC | AACTGGTGTG | AAAGAATTCT | TTGGTGAGCC 3420 |
| CCTATCTAGT | ATAGCAATCC | ACCAAGCAGG | TGAGTTCACA | CAATTCAGGT | TCTCAAAGAA 3480 |
| AATGGGCCCT | GACTTGACAG | GTATGGTCCT | TGAAGAAGGT | TGCCCTGAAG | GGACAGTCTG 3540 |
| CTCAGTCCTA | ATTAAACGGG | ATTCGGGTGA | ACTAGTTCCG | CTAGCCGTCC | GTATGGGGGC 3600 |
| TATTGCCTCC | ATGAGGATAC | AGGGTCGGCT | TGTCCATGGC | CAATCAGGGA | TGTTACTGAC 3660 |
| AGGGGCCAAT | GCAAAGGGGA | TGGATCTTGG | CACTATACCA | GGAGACTGCG | GGCACCATA 3720 |
| CGTCCACAAG | CGCGGGAATG | ACTGGGTTGT | GTGTGGAGTC | CACGCTGCAG | CCACAAAGTC 3780 |
| AGGCAACACC | GTGGTCTGCG | CTGTACAGGC | TGGAGAGGGC | GAAACCGCAC | TAGAAGGTGG 3840 |
| AGACAAGGGG | CATTATGCCG | GCCACGAGAT | TGTGAGGTAT | GGAAGTGGCC | CAGCACTGTC 3900 |
| AACTAAAACA | AAATTCTGGA | GGTCCTCCCC | AGAACCACTG | CCCCCGGAG | TATATGAGCC 3960 |
| AGCATACCTG | GGGGGCAAGG | ACCCCGGTGT | ACAGAATGGC | CCATCCCTAC | AACAGGTACT 4020 |
| ACGTGACCAA | CTGAAACCCT | TGCGGACCC | CCGCGGCCGC | ATGCCTGAGC | CTGGCCTACT 4080 |
| GGAGGCTGCG | GTTGAGACTG | TAACATCCAT | GTTAGAACAG | ACAATGGATA | CCCCAAGCCC 4140 |
| GTGGTCTTAC | GCTGATGCCT | GCCAATCTCT | TGACAAAACT | ACTAGTTCGG | GGTACCCTCA 4200 |
| CCATAAAAGG | AAGAATGATG | ATTGGAATGG | CACCAGCTTC | GTTGGAGAGC | TCGGTGAGCA 4260 |
| AGCTGCACAC | GCCAACAATA | TGTATGAGAA | TGCTAAACAT | ATGAAACCCA | TTTACACTGC 4320 |
| AGCCTTAAAA | GATGAACTAG | TCAAGCCAGA | AAAGATTTAT | CAAAAAGTCA | GAAGCGTCT 4380 |
| ACTATGGGGC | GCCGATCTCG | GAACAGTGGT | CAGGGCCGCC | CGGGCTTTTG | GCCCCATTTG 4440 |
| TGACGCTATA | AAATCACATG | TCATCAAATT | GCCAATAAAA | GTTGGCATGA | ACACAATAGA 4500 |
| AGATGGCCCC | CTCATCTATG | CTGAGCATGC | TAAATATAAG | AATCATTTTG | ATGCAGATTA 4560 |
| TACAGCATGG | GACTCAACAC | AAAATAGACA | AATTATGACA | GAATCCTTCT | CCATTATGTC 4620 |
| GCGCCTTACG | GCCTCACCAG | AATTGGCCGA | GGTTGTGGCC | CAAGATTTGC | TAGCACCATC 4680 |
| TGAGATGGAT | GTAGGTGATT | ATGTCATCAG | GGTCAAAGAG | GGGCTGCCAT | CTGGATTCCC 4740 |
| ATGTACTTCC | CAGGTGAACA | GCATAAATCA | CTGGATAATT | ACTCTCTGTG | CACTGTCTGA 4800 |
| GGCCACTGGT | TTATCACCTG | ATGTGGTGCA | ATCCATGTCA | TATTTCTCAT | TTATGGTGA 4860 |

TABLE 1-continued

The nucleotide sequence of Norwalk virus genome.

```
TGATGAGATT GTGTCAACTG ACATAGATTT TGACCCAGCC CGCCTCACTC AAATTCTCAA   4920
GGAATATGGC CTCAAACCAA CAAGGCCTGA CAAAACAGAA GGACCAATAC AAGTGAGGAA   4980
AAATGTGGAT GGACTGGTCT TCTTGCGGCG CACCATTTCC CGTGATGCGG CAGGGTTCCA   5040
AGGCAGGTTA GATAGGGCTT CGATTGAACG CCAAATCTTC TGGACCCGCG GGCCCAATCA   5100
TTCAGATCCA TCAGAGACTC TAGTGCCACA CACTCAAAGA AAAATACAGT TGATTTCACT   5160
TCTAGGGGAA GCTTCACTCC ATGGTGAGAA ATTTTACAGA AAGATTTCCA GCAAGGTCAT   5220
ACATGAAATC AAGACTGGTG GATTGGAAAT GTATGTCCCA GGATGGCAGG CCATGTTCCG   5280
CTGGATGCGC TTCCATGACC TCGGATTGTG GACAGGAGAT CGCGATCTTC TGCCCGAATT   5340
CGTAAATGAT GATGGCGTCT AAGGACGCTA CATCAAGCGT GGATGGCGCT AGTGGCGCTG   5400
GTCAGTTGGT ACCGGAGGTT AATGCTTCTG ACCCTCTTGC AATGGATCCT GTAGCAGGTT   5460
CTTCGACAGC AGTCGCGACT GCTGGACAAG TTAATCCTAT TGATCCCTGG ATAATTAATA   5520
ATTTTGTGCA AGCCCCCCAA GGTGAATTTA CTATTTCCCC AAATAATACC CCCGGTGATG   5580
TTTTGTTTGA TTTGAGTTTG GGTCCCCATC TTAATCCTTT CTTGCTCCAT CTATCACAAA   5640
TGTATAATGG TTGGGTTGGT AACATGAGAG TCAGGATTAT GCTAGCTGGT AATGCCTTTA   5700
CTGCGGGGAA GATAATAGTT TCCTGCATAC CCCCTGGTTT TGGTTCACAT AATCTTACTA   5760
TAGCACAAGC AACTCTCTTT CCACATGTGA TTGCTGATGT TAGGACTCTA GACCCCATTG   5820
AGGTGCCTTT GGAAGATGTT AGGAATGTTC TCTTTCATAA TAATGATAGA AATCAACAAA   5880
CCATGCGCCT TGTGTGCATG CTGTACACCC CCCTCCGCAC TGGTGGTGGT ACTGGTGATT   5940
CTTTTGTAGT TGCAGGGCGA GTTATGACTT GCCCCAGTCC TGATTTTAAT TTCTTGTTTT   6000
TAGTCCCTCC TACGGTGGAG CAGAAAACCA GGCCCTTCAC ACTCCCAAAT CTGCCATTGA   6060
GTTCTCTGTC TAACTCACGT GCCCCTCTCC CAATCAGTAG TATGGGCATT TCCCCAGACA   6120
ATGTCCAGAG TGTGCAGTTC CAAAATGGTC GGTGTACTCT GGATGGCCGC CTGGTTGGCA   6180
CCACCCCAGT TTCATTGTCA CATGTTGCCA AGATAAGAGG GACCTCCAAT GGCACTGTAA   6240
TCAACCTTAC TGAATTGGAT GGCACACCCT TTCACCCTTT TGAGGGCCCT GCCCCCATTG   6300
GGTTTCCAGA CCTCGGTGGT TGTGATTGGC ATATCAATAT GACACAGTTT GGCCATTCTA   6360
GCCAGACCCA GTATGATGTA GACACCACCC CTGACACTTT TGTCCCCCAT CTTGGTTCAA   6420
TTCAGGCAAA TGGCATTGGC AGTGGTAATT ATGTTGGTGT TCTTAGCTGG ATTTCCCCCC   6480
CATCACACCC GTCTGGCTCC CAAGTTGACC TTTGGAAGAT CCCCAATTAT GGGTCAAGTA   6540
TTACGGAGGC AACACATCTA GCCCCTTCTG TATACCCCCC TGGTTTCGGA GAGGTATTGG   6600
TCTTTTTCAT GTCAAAAATG CCAGGTCCTG GTGCTTATAA TTTGCCCTGT CTATTACCAC   6660
AAGAGTACAT TCACATCTT CCTAGTGAAC AAGCCCCTAC TGTAGGTGAG CTGCCCTGC   6720
TCCACTATGT TGACCCTGAT ACCGGTCGGA ATCTTGGGGA ATTCAAAGCA TACCCTGATG   6780
GTTTCCTCAC TTGTGTCCCC AATGGGGCTA GCTCGGGTCC ACAACAGCTG CCGATCAATG   6840
GGGTCTTTGT CTTTGTTTCA TGGGTGTCCA GATTTTATCA ATTAAAGCCT GTGGGAACTG   6900
CCAGCTCGGC AAGAGGTAGG CTTGGTCTGC GCCGATAATG GCCCAAGCCA TAATTGGTGC   6960
AATTGCTGCT TCCACAGCAG GTAGTGCTCT GGGAGCGGGC ATACAGGTTG GTGGCGAAGC   7020
GGCCCTCCAA AGCCAAAGGT ATCAACAAAA TTTGCAACTG CAAGAAAATT CTTTTAAACA   7080
TGACAGGGAA ATGATTGGGT ATCAGGTTGA AGCTTCAAAT CAATTATTGG CTAAAAATTT   7140
GGCAACTAGA TATTCACTCC TCCGTGCTGG GGGTTTGACC AGTGCTGATG CAGCAAGATC   7200
```

TABLE 1-continued

The nucleotide sequence of Norwalk virus genome.

```
TGTGGCAGGA GCTCCAGTCA CCCGCATTGT AGATTGGAAT GGCGTGAGAG TGTCTGCTCC 7260

CGAGTCCTCT GCTACCACAT TGAGATCCGG TGGCTTCATG TGAGTTCCCA TACCATTTGC 7320

CTCTAAGCAA AAACAGGTTC AATCATCTGG TATTAGTAAT CCAAATTATT CCCCTTCATC 7380

CATTTCTCGA ACCACTAGTT GGGTCGAGTC ACAAAACTCA TCGAGATTTG GAAATCTTTC 7440

TCCATACCAC GCGGAGGCTC TCAATACAGT GTGGTTGACT CCACCCGGTT CAACAGCCTC 7500

TTCTACACTG TCTTCTGTGC CACGTGGTTA TTTCAATACA GACAGGTTGC CATTATTCGC 7560

AAATAATAGG CGATGATGTT GTAATATGAA ATGTGGGCAT CATATTCATT TAATTAGGTT 7620

TAATTAGGTT TAATTTGATG TTAAAAAAAA AAAAAAAAAA AAAAAAAAAA AAAAAAAAAA 7680

AAAAAAAAAA AAAAAAAAAA AAAAAAAAAA AAAAAAAAAA AAAA              7724
```

TABLE 2

The amino acid sequence deduced from nucleotides 146 through 5359 of the Norwalk virus genome shown in Table 1.

```
CTCGATAAAG ATAACCAACC AAGAT ATG GCT CTG GGG CTG ATT GGA CAG GTC  172
                            Met Ala Leu Gly Leu Ile Gly Gln Val
                             1           5

CCA GCG CCA AAG GCC ACA TCC GTC GAT GTC CCT AAA CAA CAG AGG GAT  220
Pro Ala Pro Lys Ala Thr Ser Val Asp Val Pro Lys Gln Gln Arg Asp
 10              15                  20                  25

AGA CCA CCA CGG ACT GTT GCC GAA GTT CAA CAA AAT TTG CGT TGG ACT  268
Arg Pro Pro Arg Thr Val Ala Glu Val Gln Gln Asn Leu Arg Trp Thr
             30                  35                  40

GAG AGA CCA CAA GAC CAG AAT GTT AAG ACG TGG GAT GAG CTT GAC CAC  316
Glu Arg Pro Gln Asp Gln Asn Val Lys Thr Trp Asp Glu Leu Asp His
         45                  50                  55

ACA ACA AAA CAA CAG ATA CTT GAT GAA CAC GCT GAG TGG TTT GAT GCC  364
Thr Thr Lys Gln Gln Ile Leu Asp Glu His Ala Glu Trp Phe Asp Ala
     60                  65                  70

GGT GGC TTA GGT CCA AGT ACA CTA CCC ACT AGT CAT GAA CGG TAC ACA  412
Gly Gly Leu Gly Pro Ser Thr Leu Pro Thr Ser His Glu Arg Tyr Thr
 75                  80                  85

CAT GAG AAT GAT GAA GGC CAC CAG GTA AAG TGG TCG GCT AGG GAA GGT  460
His Glu Asn Asp Glu Gly His Gln Val Lys Trp Ser Ala Arg Glu Gly
 90                  95                 100                 105

GTA GAC CTT GGC ATA TCC GGG CTC ACG ACG GTG TCT GGG CCT GAG TGG  508
Val Asp Leu Gly Ile Ser Gly Leu Thr Thr Val Ser Gly Pro Glu Trp
                 110                 115                 120

AAT ATG TGC CCG CTA CCA CCA GTT GAC CAA AGG AGC ACG ACA CCT GCA  556
Asn Met Cys Pro Leu Pro Pro Val Asp Gln Arg Ser Thr Thr Pro Ala
             125                 130                 135

ACT GAG CCC ACA ATT GGT GAC ATG ATC GAA TTC TAT GAA GGG CAC ATC  604
Thr Glu Pro Thr Ile Gly Asp Met Ile Glu Phe Tyr Glu Gly His Ile
         140                 145                 150

TAT CAT TAT GCT ATA TAC ATA GGT CAA GGC AAG ACG GTG GGT GTA CAC  652
Tyr His Tyr Ala Ile Tyr Ile Gly Gln Gly Lys Thr Val Gly Val His
     155                 160                 165

TCC CCT CAA GCA CCC TTC TCA ATA ACG AGG ATC ACC ATA CAG CCC ATA  700
Ser Pro Gln Ala Pro Phe Ser Ile Thr Arg Ile Thr Ile Gln Pro Ile
 170                 175                 180                 185
```

TABLE 2-continued

The amino acid sequence deduced from nucleotides 146 through 5359 of the Norwalk virus genome shown in Table 1.

```
TCA GCT TGG TGG CGA GTC TGT TAT GTC CCA CAA CCA AAA CAG AGG CTC   748
Ser Ala Trp Trp Arg Val Cys Tyr Val Pro Gln Pro Lye Gln Arg Leu
            190                 195                 200

ACA TAC GAC CAA CTC AAA GAA TTA GAA AAT GAA CCA TGG CCG TAT GCC   796
Thr Tyr Asp Gln Leu Lys Glu Leu Glu Asn Glu Pro Trp Pro Tyr Ala
                205                 210                 215

GCA GTC ACG AAC AAC TGC TTC GAA TTT TGT TGC CAG GTC ATG TGC TTG   844
Ala Val Thr Asn Asn Cys Phe Glu Phe Cys Cys Gln Val Met Cys Leu
                220                 225                 230

GAA GAT ACT TGG TTG CAA AGG AAG CTC ATC TCC TCT GGC CGG TTT TAC   892
Glu Asp Thr Trp Leu Gln Arg Lye Leu Ile Ser Ser Gly Arg Phe Tyr
            235                 240                 245

CAC CCG ACC CAA GAT TGG TCC CGA GAC ACT CCA GAA TTC CAA CAA GAC   940
His Pro Thr Gln Asp Trp Ser Arg Asp Thr Pro Glu Phe Gln Gln Asp
250                 255                 260                 265

AGC AAG TTA GAG ATG GTT AGG GAT GCA GTG CTA GCC GCT ATA AAT GGG   988
Ser Lys Leu Glu Met Val Arg Asp Ala Val Leu Ala Ala Ile Asn Gly
                270                 275                 280

TTG GTG TCG CGG CCA TTT AAA GAT CTT CTG GGT AAG CTC AAA CCC TTG  1036
Leu Val Ser Arg Pro Phe Lys Asp Leu Leu Gly Lys Leu Lys Pro Leu
            285                 290                 295

AAC GTG CTT AAC TTA CTT TCA AAC TGT GAT TGG ACG TTC ATG GGG GTC  1084
Asn Val Leu Asn Leu Leu Ser Asn Cys Asp Trp Thr Phe Met Gly Val
                300                 305                 310

GTG GAG ATG GTG GTC CTC CTT TTA GAA CTC TTT GGA ATC TTT TGG AAC  1132
Val Glu Met Val Val Leu Leu Leu Glu Leu Phe Gly Ile Phe Trp Asn
            315                 320                 325

CCA CCT GAT GTT TCC AAC TTT ATA GCT TCA CTC CTG CCA GAT TTC CAT  1180
Pro Pro Asp Val Ser Asn Phe Ile Ala Ser Leu Leu Pro Asp Phe His
330                 335                 340                 345

CTA CAG GGC CCC GAG GAC CTT GCC AGG GAT CTC GTG CCA ATA GTA TTG  1228
Leu Gln Gly Pro Glu Asp Leu Ala Arg Asp Leu Val Pro Ile Val Leu
                350                 355                 360

GGG GGG ATC GGC TTA GCC ATA GGA TTC ACC AGA GAC AAG GTA AGT AAG  1276
Gly Gly Ile Gly Leu Ala Ile Gly Phe Thr Arg Asp Lys Val Ser Lys
            365                 370                 375

ATG ATG AAG AAT GCT GTT GAT GGA CTT CGT GCG GCA ACC CAG CTC GGT  1324
Met Met Lys Asn Ala Val Asp Gly Leu Arg Ala Ala Thr Gln Leu Gly
            380                 385                 390

CAA TAT GGC CTA GAA ATA TTC TCA TTA CTA AAG AAG TAC TTC TTC GGT  1372
Gln Tyr Gly Leu Glu Ile Phe Ser Leu Leu Lys Lys Tyr Phe Phe Gly
395                 400                 405

GGT GAT CAA ACA GAG AAA ACC CTA AAA GAT ATT GAG TCA GCA GTT ATA  1420
Gly Asp Gln Thr Glu Lys Thr Leu Lys Asp Ile Glu Ser Ala Val Ile
410                 415                 420                 425

GAT ATG GAA GTA GTA TCA TCT ACA TCA GTG ACT CAG CTC GTG AGG GAC  1468
Asp Met Glu Val Leu Set Ser Thr Set Val Thr Gln Leu Val Arg Asp
                430                 435                 440

AAA CAG TCT GCA CGG GCT TAT ATG GCC ATC TAA GAT AAT GAA GAA GAA  1516
Lys Gln Ser Ala Arg Ala Tyr Met Ala Ile Leu Asp Asn Glu Glu Glu
            445                 450                 455

AAG GCA AGG AAA TTA TCT GTC AGG AAT GCC GAC CCA CAC GTA GTA TCC  1564
Lys Ala Arg Lys Leu Ser Val Arg Asn Ala Asp Pro His Val Val Ser
            460                 465                 470

TCT ACC AAT GCT CTC ATA TCC CGG ATC TCA ATG GCT AGG GCT GCA TTG  1612
Ser Thr Asn Ala Leu lIe Ser Arg Ile Ser Met Ala Arg Ala Ala Leu
            475                 480                 485
```

TABLE 2-continued

The amino acid sequence deduced from nucleotides 146 through 5359 of the Norwalk virus genome shown in Table 1.

```
GCC AAG GCT CAA GCT GAA ATG ACC AGC AGG ATG CGT CCT GTG GTC ATT  1660
Ala Lys Ala Gln Ala Glu Met Thr Ser Arg Met Arg Pro Val Val Ile
490             495                 500                 505

ATG ATG TGT GGG CCC CCT GGT ATA GGT AAA ACC AAG GCA GCA GAA CAT  1708
Met Met Cys Gly Pro Pro Gly Ile Gly Lys Thr Lys Ala Ala Glu His
                510                 515                 520

CTG GCT AAA CGC CTA GCC AAT GAG ATA CGG CCT GGT GGT AAG GTT GGG  1756
Leu Ala Lys Arg Leu Ala Asn Glu Ile Arg Pro Gly Gly Lys Val Gly
            525                 530                 535

CTG GTC CCA CGG GAG GCA GTG GAT CAT TGG GAT GGA TAT CAC GGA GAG  1804
Leu Val Pro Arg Glu Ala Val Asp His Trp Asp Gly Tyr His Gly Glu
        540                 545                 550

GAA GTG ATG CTG TGG GAC GAG TAT GGA ATG ACA AAG ATA CAG GAA GAC  1852
Glu Val Met Leu Trp Asp Glu Tyr Gly Met Thr Lys Ile Gln Glu Asp
    555                 560                 565

TGT AAT AAA CTG CAA GCC ATA GCC GAC TCA GCC CCC CTA ACA CTC AAT  1900
Cys Asn Lys Leu Gln Ala Ile Ala Asp Ser Ala Pro Leu Thr Leu Asn
570                 575                 580                 585

TGT GAC CGA ATA GAA AAC AAG GGA ATG CAA TTT GTG TGT GAT GCT ATA  1948
Cys Asp Arg Ile Glu Asn Lys Gly Met Gln Phe Val Cys Asp Ala Ile
                590                 595                 600

GTC ATC ACC ACC AAT GCT CCT GGC CCA GCC CCA GTG GAC TTT GTC AAC  1996
Val Ile Thr Thr Asn Ala Pro Gly Pro Ala Pro Val Asp Phe Val Asn
            605                 610                 615

CTC GGG CCT GTT TGC CGA AGG GTG GAC TTC CTT GTG TAT TGC ACG GCA  2044
Leu Gly Pro Val Cys Arg Arg Val Asp Phe Leu Val Tyr Cys Thr Ala
        620                 625                 630

CGT GAA GTT GAA CAC ACG AGG AAA GTC AGT CCT GGG GAC ACA ACT GCA  2092
Pro Glu Val Glu His Thr Arg Lys Val Ser Pro Gly Asp Thr Thr Ala
    635                 640                 645

CTG AAA GAC TGC TTC AAG CCC GAT TTC TCA CAT CTA AAA ATG GAG TTG  2140
Leu Lys Asp Cys Phe Lys Pro Asp Phe Ser His Leu Lys Met Glu Leu
650                 655                 660                 665

GCT CCC CAA GGG GGC TTT GAT AAC CAA GGG AAT ACC CCG TTT GGT AAG  2188
Ala Pro Gln Gly Gly Phe Asp Asn Gln Gly Asn Thr Pro Phe Gly Lys
                670                 675                 680

GGT GTG ATG AAG CCC ACC ACC ATA AAC AGG CTG TTA ATC CAG GCT GTA  2236
Gly Val Met Lys Pro Thr Thr Ile Asn Arg Leu Leu Ile Gln Ala Val
            685                 690                 695

GCC TTG ACG ATG GAG AGA CAG GAT GAG TTC CAA CTC CAG GGG CCT ACG  2284
Ala Leu Thr Met Glu Arg Gln Asp Glu Phe Gln Leu Gln Gly Pro Thr
        700                 705                 710

TAT GAC TTT GAT ACT GAC AGA GTA GCT GCG TTC ACG AGG ATG GCC CGA  2332
Tyr Asp Phe Asp Thr Asp Arg Val Ala Ala Phe Thr Arg Met Ala Arg
    715                 720                 725

GCC AAC GGG TTG GGT CTC ATA TCC ATG GCC TCC CTA GGC AAA AAG CTA  2380
Ala Asn Gly Leu Gly Leu Ile Ser Met Ala Ser Leu Gly Lys Lys Leu
730                 735                 740                 745

CGC AGT GTC ACC ACT ATT GAA GGA TTA AAG AAT GCT CTA TCA GGC TAT  2428
Arg Ser Val Thr Thr Ile Glu Gly Leu Lys Asn Ala Leu Ser Gly Tyr
                750                 755                 760

AAA ATA TCA AAA TGC AGT ATA CAA TGG CAG TCA AGG GTG TAC ATT ATA  2476
Lys Ile Ser Lys Cys Ser Ile Gln Trp Gln Ser Arg Val Tyr Ile Ile
            765                 770                 775

GAA TCA GAT GGT GCC AGT GTA CAA ATC AAA GAA GAC AAG CAA GCT TTG  2524
Glu Ser Asp Gly Ala Ser Val Gln Ile Lys Glu Asp Lys Gln Ala Leu
        780                 785                 790
```

TABLE 2-continued

The amino acid sequence deduced from nucleotides 146 through 5359 of the Norwalk virus genome shown in Table 1.

```
ACC CCT CTG CAG CAG ACA ATT AAC ACG GCC TCA CTT GCC ATC ACT CGA   2572
Thr Pro Leu Gln Gln Thr Ile Asn Thr Ala Ser Leu Ala Ile Thr Arg
795                 800                 805

CTC AAA GCA GCT AGG GCT GTG GCA TAC GCT TCA TGT TTC CAG TCC GCC   2620
Leu Lys Ala Ala Arg Ala Val Ala Tyr Ala Ser Cys Phe Gln Ser Ala
810                 815                 820                 825

ATA ACT ACC ATA CTA CAA ATG GCG GGA TCT GCG CTC GTT ATT AAT CGA   2668
Ile Thr Thr Ile Leu Gln Met Ala Gly Ser Ala Leu Val Ile Asn Arg
                830                 835                 840

GCG GTC AAG CGT ATG TTT GGT ACC CGT ACA GCA GCC ATG GCA TTA GAA   2716
Ala Val Lys Arg Met Phe Gly Thr Arg Thr Ala Ala Met Ala Leu Glu
            845                 850                 855

GGA CCT GGG AAA GAA CAT AAT TGC AGG GTC CAT AAG GCT AAG GAA GCT   2764
Gly Pro Gly Lys Glu His Asn Cys Arg Val His Lys Ala Lys Glu Ala
        860                 865                 870

GGA AAG GGG CCC ATA GGT CAT GAT GAC ATG GTA GAA AGG TTT GCC CTA   2812
Gly Lys Gly Pro Ile Gly His Asp Asp Met Val Glu Arg Phe Gly Leu
875                 880                 885

TGT GAA ACT GAA GAG GAG GAG AGT GAG GAC CAA ATT CAA ATG GTA CCA   2860
Cys Glu Thr Glu Glu Glu Glu Ser Glu Asp Gln Ile Gln Met Val Pro
890                 895                 900                 905

ACT GAT GCC GTC CCA GAA GGA AAG AAC AAA GGC AAG ACC AAA AAG GGA   2908
Ser Asp Ala Val Pro Glu Gly Lys Asn Lys Gly Lys Thr Lys Lys Gly
                910                 915                 920

CGT GGT CGC AAA AAT AAC TAT AAT GCA TTC TCT CGC CGT GGT CTG AGT   2956
Arg Gly Arg Lys Asn Asn Tyr Asn Ala Phe Ser Arg Arg Gly Leu Ser
            925                 930                 935

GAT GAA GAA TAT GAA GAG TAC AAA AAG ATC AGA GAA GAA AAG AAT GGC   3004
Asp Glu Glu Tyr Glu Glu Tyr Lys Lys Ile Arg Glu Glu Lys Asn Gly
        940                 945                 950

AAT TAT AGT ATA CAA GAA TAC TTG GAG GAC CGC CAA CGA TAT GAG GAA   3052
Asn Tyr Ser Ile Gln Glu Tyr Leu Clu Asp Arg Gln Arg Tyr Glu Glu
955                 960                 965

GAA TTA GCA GAG GTA CAG GCA GGT GGT GAT GGT GGC ATA GGA GAA ACT   3100
Glu Leu Ala Glu Val Gln Ala Gly Gly Asp Gly Gly Ile Gly Glu Thr
970                 975                 980                 985

GAA ATG GAA ATC CGT CAC AGG GTC TTC TAT AAA TCC AAG AGT AAG AAA   3148
Glu Met Glu Ile Arg His Arg Val Phe Tyr Lys Ser Lys Ser Lys Lys
                990                 995                 1000

CAC CAA CAA GAG CAA CGG CGA CAA CTT GGT CTA GTG ACT GGA TCA GAC   3196
His Gln Gln Glu Gln Arg Arg Gln Leu Gly Leu Val Thr Gly Ser Asp
            1005                1010                1015

ATC AGA AAA CGT AAG CCC ATT GAC TGG ACC CCG CCA AAG AAT GAA TGG   3244
Ile Arg Lys Arg Lys Pro Ile Asp Trp Thr Pro Pro Lys Asn Glu Trp
        1020                1025                1030

GCA GAT GAT GAC AGA GAG GTG GAT TAT AAT GAA AAG ATC AAT TTT GAA   3292
Ala Asp Asp Asp Arg Glu Val Asp Tyr Asn Glu Lys Ile Asn Phe Glu
1035                1040                1045

GCT CCC CCG ACA CTA TGG AGC CGA GTC ACA AAG TTT GGA TCA GGA TGG   3340
Ala Pro Pro Thr Leu Trp Ser Arg Val Thr Lys Phe Gly Ser Gly Trp
1050                1055                1060                1065

GGC TTT TGG GTC AGC CCG ACA GTG TTC ATC ACA ACC ACA CAT GTA GTG   3388
Gly Phe Trp Val Ser Pro Thr Val Phe Ile Thr Thr Thr His Val Val
                1070                1075                1080

CCA ACT GGT GTG AAA GAA TTC TTT GGT GAG CCC CTA TCT AGT ATA GCA   3436
Pro Thr Gly Val Lys Glu Phe Phe Gly Glu Pro Leu Ser Ser Ile Ala
            1085                1090                1095
```

TABLE 2-continued

The amino acid sequence deduced from nucleotides 146 through 5359 of the Norwalk virus genome shown in Table 1.

```
ATC CAC CAA GCA GGT GAG TTC ACA CAA TTC AGG TTC TCA AAG AAA ATG   3484
Ile His Gln Ala Gly Glu Phe Thr Gln Phe Arg Phe Ser Lys Lys Met
        1100            1105            1110

CGC CCT GAC TTG ACA GGT ATG GTC CTT GAA GAA GGT TGC CCT GAA GGG   3532
Arg Pro Asp Leu Thr Gly Met Val Leu Glu Glu Gly Cys Pro Glu Gly
    1115            1120            1125

ACA GTC TGC TCA GTC CTA ATT AAA CGG GAT TCG GGT GAA CTA CTT CCG   3580
Thr Val Cys Ser Val Leu Ile Lys Arg Asp Ser Gly Glu Leu Leu Pro
1130            1135            1140            1145

CTA GCC GTC CGT ATG GGG GCT ATT GCC TCC ATG AGG ATA CAG GGT CGG   3628
Leu Ala Val Arg Met Gly Ala Ile Ala Ser Met Arg Ile Gln Gly Arg
            1150            1155            1160

CTT GTC CAT GGC CAA TCA GGG ATG TTA CTG ACA GGG GCC AAT GCA AAG   3676
Leu Val His Gly Gln Ser Gly Met Leu Leu Thr Gly Ala Asn Ala Lys
        1165            1170            1175

GGG ATG GAT CTT GGC ACT ATA CCA GGA GAC TGC GGG GCA CCA TAC GTC   3724
Gly Met Asp Leu Gly Thr Ile Pro Gly Asp Cys Gly Ala Pro Tyr Val
        1180            1185            1190

CAC AAG CGC GGG AAT GAG TGG GTT GTG TGT GGA GTC CAC GCT GCA GCC   3772
His Lys Arg Gly Asn Glu Trp Val Val Cys Gly Val His Ala Ala Ala
    1195            1200            1205

ACA AAG TCA GGC AAC ACC GTG GTC TGC GCT GTA CAG GCT GGA GAG GGC   3820
Thr Lys Ser Gly Asn Thr Val Val Cys Ala Val Gln Ala Gly Glu Gly
1210            1215            1220            1225

GAA ACC GCA CTA GAA GGT GGA GAC AAG GGG CAT TAT GCC GGC CAC GAG   3868
Glu Thr Ala Leu Glu Gly Gly Asp Lys Gly His Tyr Ala Gly His Glu
            1230            1235            1240

ATT GTG AGG TAT GGA AGT GGC CCA GCA CTG TCA ACT AAA ACA AAA TTC   3916
Ile Val Arg Tyr Gly Ser Gly Pro Ala Leu Ser Thr Lys Thr Lys Phe
            1245            1250            1255

TGG AGG TCC TCC CCA GAA CCA CTG CCC CCC GGA GTA TAT GAG CCA GCA   3964
Trp Arg Ser Ser Pro Glu Pro Leu Pro Pro Gly Val Tyr Glu Pro Ala
1260            1265            1270

TAC CTG GGG GGC AAG GAC CCC CGT GTA CAG AAT GGC CCA TCC CTA CAA   4012
Tyr Leu Gly Gly Lys Asp Pro Arg Val Gln Asn Gly Pro Ser Leu Gln
        1275            1280            1285

CAG GTA CTA CGT GAC CAA CTG AAA CCC TTT GCG GAG CCC CGC GGC CGC   4060
Gln Val Leu Arg Asp Gln Leu Lys Pro Phe Ala Glu Pro Arg Gly Arg
1290            1295            1300            1305

ATG CCT GAG CCT GGC CTA CTG GAG GCT GCG GTT GAG ACT GTA ACA TCC   4108
Met Pro Glu Pro Gly Leu Leu Glu Ala Ala Val Glu Thr Val Thr Ser
            1310            1315            1320

ATG TTA GAA CAG ACA ATG GAT ACC CCA AGC CCG TGG TCT TAC GCT GAT   4156
Met Leu Glu Gln Thr Met Asp Thr Pro Ser Pro Trp Ser Tyr Ala Asp
            1325            1330            1335

GCC TGC CAA TCT CTT GAC AAA ACT ACT AGT TCG GGG TAC CCT CAC CAT   4204
Ala Cys Gln Ser Leu Asp Lys Thr Thr Ser Ser Gly Tyr Pro His His
        1340            1345            1350

AAA AGG AAG AAT GAT GAT TGG AAT GGC ACC ACC TTC GTT GGA GAG CTC   4252
Lys Arg Lys Asn Asp Asp Trp Asn Gly Thr Thr Phe Val Gly Glu Leu
        1355            1360            1365

GGT GAG CAA GCT GCA CAC GCC AAC AAT ATG TAT GAG AAT GCT AAA CAT   4300
Gly Glu Gln Ala Ala His Ala Asn Asn Met Tyr Glu Asn Ala Lys His
1370            1375            1380            1385

ATG AAA CCC ATT TAC ACT GCA GCC TTA AAA GAT GAA CTA GTC AAG CCA   4348
Met Lys Pro Ile Tyr Thr Ala Ala Leu Lys Asp Glu Leu Val Lys Pro
            1390            1395            1400
```

TABLE 2-continued

The amino acid sequence deduced from nucleotides 146 through 5359 of the Norwalk virus genome shown in Table 1.

```
GAA AAG ATT TAT CAA AAA GTC AAG AAG CGT CTA CTA TGG GGC GCC GAT   4396
Glu Lys Ile Tyr Gln Lys Val Lys Lys Arg Leu Leu Trp Gly Ala Asp
            1405                1410                1415

CTC GGA ACA GTG GTC AGG GCC GCC CGG GCT TTT GGC CCA TTT TGT GAC   4444
Leu Gly Thr Val Val Arg Ala Ala Arg Ala Phe Gly Pro Phe Cys Asp
            1420                1425                1430

GCT ATA AAA TCA CAT GTC ATC AAA TTG CCA ATA AAA GTT GGC ATG AAC   4492
Ala Ile Lys Ser His Val Ile Lys Leu Pro Ile Lys Val Gly Met Asn
            1435                1440                1445

ACA ATA GAA GAT GGC CCC CTC ATC TAT GCT GAG CAT GCT AAA TAT AAG   4540
Thr Ile Glu Asp Gly Pro Leu Ile Tyr Ala Glu His Ala Lys Tyr Lys
1450                1455                1460                1465

AAT CAT TTT GAT GCA GAT TAT ACA GCA TGG GAC TCA ACA CAA AAT AGA   4588
Asn His Phe Asp Ala Asp Tyr Thr Ala Trp Asp Ser Thr Gln Asn Arg
                1470                1475                1480

CAA ATT ATG ACA GAA TCC TTC TCC ATT ATG TCG CGC CTT ACG GCC TCA   4636
Gln Ile Met Thr Glu Ser Phe Ser Ile Met Ser Arg Leu Thr Ala Ser
            1485                1490                1495

CCA GAA TTG GCC GAG GTT GTG GCC CAA GAT TTG CTA GCA CCA TCT GAG   4684
Pro Glu Leu Ala Glu Val Val Ala Gln Asp Leu Leu Ala Pro Ser Glu
            1500                1505                1510

ATG GAT GTA GGT GAT TAT GTC ATC AGG GTC AAA GAG GGG CTG CCA TCT   4732
Met Asp Val Gly Asp Tyr Val Ile Arg Val Lys Glu Gly Leu Pro Ser
            1515                1520                1525

GGA TTC CCA TGT ACT TCC CAG GTG AAC AGC ATA AAT CAC TGG ATA ATT   4780
Gly Phe Pro Cys Thr Ser Gln Val Asn Ser Ile Asn His Trp Ile Ile
1530                1535                1540                1545

ACT CTC TGT GCA CTG TCT GAG GCC ACT GGT TTA TCA CCT GAT GTG GTG   4828
Thr Leu Cys Ala Leu Ser Glu Ala Thr Gly Leu Ser Pro Asp Val Val
                1550                1555                1560

CAA TCC ATG TCA TAT TTC TCA TTT TAT GGT GAT GAT GAG ATT GTG TCA   4876
Gln Ser Met Ser Tyr Phe Ser Phe Tyr Gly Asp Asp Glu Ile Val Ser
            1565                1570                1575

ACT GAC ATA GAT TTT GAC CCA GCC CGC CTC ACT CAA ATT CTC AAG GAA   4924
Thr Asp Ile Asp Phe Asp Pro Ala Arg Leu Thr Gln Ile Leu Lys Glu
            1580                1585                1590

TAT GGC CTC AAA CCA ACA AGG CCT GAC AAA ACA GAA GGA CCA ATA CAA   4972
Tyr Gly Leu Lys Pro Thr Arg Pro Asp Lys Thr Glu Gly Pro Ile Gln
            1595                1600                1605

GTG AGG AAA AAT GTG GAT GGA CTG GTC TTC TTG CGG CGC ACC ATT TCC   5020
Val Arg Lys Asn Val Asp Gly Leu Val Phe Leu Arg Arg Thr Ile Ser
1610                1615                1620                1625

CGT GAT GCG GCA GGG TTC CAA GGC AGG TTA GAT AGG GCT TCG ATT GAA   5068
Arg Asp Ala Ala Gly Phe Gln Gly Arg Leu Asp Arg Ala Ser Ile Glu
                1630                1635                1640

CGC CAA ATC TTC TGG ACC CGC GGG CCC AAT CAT TCA GAT CCA TCA GAG   5116
Arg Gln Ile Phe Trp Thr Arg Gly Pro Asn His Ser Asp Pro Ser Glu
            1645                1650                1655

ACT CTA GTG CCA CAC ACT CAA AGA AAA ATA CAG TTG ATT TCA CTT CTA   5164
Thr Leu Val Pro His Thr Gln Arg Lys Ile Gln Leu Ile Ser Leu Leu
            1660                1665                1670

GGG GAA GCT TCA CTC CAT GGT GAG AAA TTT TAC AGA AAG ATT TCC AGC   5212
Gly Glu Ala Ser Leu His Gly Glu Lys Phe Tyr Arg Lys Ile Ser Ser
            1675                1680                1685

AAG GTC ATA CAT GAA ATC AAG ACT GGT GGA TTG GAA ATG TAT GTC CCA   5260
Lys Val Ile His Glu Ile Lys Thr Gly Gly Leu Glu Met Tyr Val Pro
1690                1695                1700                1705
```

TABLE 2-continued

The amino acid sequence deduced from nucleotides 146 through 5359 of the Norwalk virus genome shown in Table 1.

```
GGA TGG CAG GCC ATG TTC CGG TGG ATG CGC TTC CAT GAC CTC GGA TTG   5308
Gly Trp Gln Ala Met Phe Arg Trp Met Arg Phe His Asp Leu Gly Leu
            1710                1715                1720

TGG ACA GGA GAT CGG GAT CTT CTG CCC GAA TTC GTA AAT GAT GAT GGC   5356
Trp Thr Gly Asp Arg Asp Leu Leu Pro Glu Phe Val Asn Asp Asp Gly
            1725                1730                1735

GTC TAAGGACGCT ACATCAAGCG TGGATGGCGC TAGTGGCGCT GGTCAGTTGG        5409
Val
```

TABLE 3

The amino acid sequence deduced from nucleotides 5346 through 6935 of the Norwalk virus genome shown in Table 1.

```
CGTAA ATG ATG ATG GCG TCT AAG GAC GCT ACA TCA AGC GTG GAT GGC   5387
      Met Met Met Ala Ser Lys Asp Ala Thr Ser Ser Val Asp Gly
      1               5                   10

GCT AGT GGC GCT GGT CAG TTG GTA CCG GAG GTT AAT GCT TCT GAC CCT   5435
Ala Ser Gly Ala Gly Gln Leu Val Pro Glu Val Asn Ala Ser Asp Pro
15              20                  25                  30

CTT GCA ATG GAT CCT GTA GCA GGT TCT TCG ACA GCA GTC GCG ACT GCT   5483
Leu Ala Met Asp Pro Val Ala Gly Ser Ser Thr Ala Val Ala Thr Ala
                35                  40                  45

GGA CAA GTT AAT CCT ATT GAT CCC TGG ATA ATT AAT AAT TTT GTG CAA   5531
Gly Gln Val Asn Pro Ile Asp Pro Trp Ile Ile Asn Asn Phe Val Gln
            50                  55                  60

GCC CCC CAA GGT GAA TTT ACT ATT TCC CCA AAT AAT ACC CCC GGT GAT   5579
Ala Pro Gln Gly Glu Phe Thr Ile Ser Pro Asn Asn Thr Pro Gly Asp
            65                  70                  75

GTT TTG TTT GAT TTG AGT TTG GGT CCC CAT CTT AAT CCT TTC TTG CTC   5627
Val Leu Phe Asp Leu Ser Leu Gly Pro His Leu Asn Pro Phe Leu Leu
        80                  85                  90

CAT CTA TCA CAA ATG TAT AAT GGT TGG GTT GGT AAC ATG AGA GTC AGG   5675
His Leu Ser Gln Met Tyr Asn Gly Trp Val Gly Asn Met Arg Val Arg
    95                  100                 105                 110

ATT ATG CTA GCT GGT AAT GCC TTT ACT GCG GGG AAG ATA ATA GTT TCC   5723
Ile Met Leu Ala Gly Asn Ala Phe Thr Ala Gly Lys Ile Ile Val Ser
                115                 120                 125

TGC ATA CCC CCT GGT TTT GGT TCA CAT AAT CTT ACT ATA GCA CAA GCA   5771
Cys Ile Pro Pro Gly Phe Gly Ser His Asn Leu Thr Ile Ala Gln Ala
            130                 135                 140

ACT CTC TTT CCA CAT GTG ATT GCT GAT GTT AGG ACT CTA GAC CCC ATT   5819
Thr Leu Phe Pro His Val Ile Ala Asp Val Arg Thr Leu Asp Pro Ile
            145                 150                 155

GAG GTG CCT TTG GAA GAT GTT AGG AAT GTT CTC TTT CAT AAT AAT GAT   5867
Glu Val Pro Leu Glu Asp Val Arg Asn Val Leu Phe His Asn Asn Asp
            160                 165                 170

AGA AAT CAA CAA ACC ATG CGC CTT GTG TGC ATG CTG TAC ACC CCC CTC   5915
Arg Asn Gln Gln Thr Met Arg Leu Val Cys Met Leu Tyr Thr Pro Leu
175                 180                 185                 190

CGC ACT GGT GGT GGT ACT GGT GAT TGT TTT GTA GTT GCA GGG CGA GTT   5963
Arg Thr Gly Gly Gly Thr Gly Asp Cys Phe Val Val Ala Gly Arg Val
                195                 200                 205

ATG ACT TGC CCC AGT CCT GAT TTT AAT TTC TTG TTT TTA GTC GTT CCT   6011
Met Thr Cys Pro Ser Pro Asp Phe Asn Phe Leu Phe Leu Val Pro Pro
            210                 215                 220
```

TABLE 3-continued

The amino acid sequence deduced from nucleotides 5346 through 6935 of the Norwalk virus genome shown in Table 1.

```
ACG GTG GAG CAG AAA ACC AGG CCC TTC ACA CTC CCA AAT CTG CCA TTG   6059
Thr Val Glu Gln Lys Thr Arg Pro Phe Thr Leu Pro Asn Leu Pro Leu
        225                 230                 235

AGT TCT CTG TCT AAC TCA CGT GCC CCT CTC CCA ATC AGT AGT ATG GGC   6107
Ser Ser Leu Ser Asn Ser Arg Ala Pro Leu Pro Ile Ser Ser Met Gly
        240                 245                 250

ATT TCC CCA GAC AAT GTC CAG AGT GTG CAG TTC CAA AAT GGT CGG TGT   6155
Ile Ser Pro Asp Asn Val Gln Ser Val Gln Phe Gln Asn Gly Arg Cys
255                 260                 265                 270

ACT CTG GAT GGC CGC CTG GTT GGC ACC ACC CCA GTT TCA TTG TCA CAT   6203
Thr Leu Asp Gly Arg Leu Val Gly Thr Thr Pro Val Ser Leu Ser His
                275                 280                 285

GTT GCC AAG ATA AGA GGG ACC TCC AAT GGC ACT GTA ATC AAC CTT ACT   6251
Val Ala Lys Ile Arg Gly Thr Ser Asn Gly Thr Val Ile Asn Leu Thr
        290                 295                 300

GAA TTG GAT GGC ACA CCC TTT CAC CCT TTT GAG GGC CCT GCC CCC ATT   6299
Glu Leu Asp Gly Thr Pro Phe His Pro Phe Glu Gly Pro Ala Pro Ile
        305                 310                 315

GGG TTT CCA GAC CTC GGT GGT TGT GAT TGG CAT ATC AAT ATG ACA CAG   6347
Gly Phe Pro Asp Leu Gly Gly Cys Asp Trp His Ile Asn Met Thr Gln
320                 325                 330

TTT GGC CAT TCT AGC CAG ACC CAG TAT GAT GTA GAC ACC ACC CCT GAC   6395
Phe Gly His Ser Ser Gln Thr Gln Tyr Asp Val Asp Thr Thr Pro Asp
335                 340                 345                 350

ACT TTT GTC CCC CAT CTT GGT TCA ATT CAG GCA AAT GGC ATT GGC AGT   6443
Thr Phe Val Pro His Leu Gly Ser Ile Gln Ala Asn Gly Ile Gly Ser
                355                 360                 365

GGT AAT TAT GTT GGT GTT GTT AGC TGG ATT TCC CCC CCA TCA CAC CCG   6491
Gly Asn Tyr Val Gly Val Leu Ser Trp Ile Ser Pro Pro Ser His Pro
        370                 375                 380

TCT GGC TCC CAA GTT GAC CTT TGG AAG ATC CCC AAT TAT GGG TCA AGT   6539
Ser Gly Ser Gln Val Asp Leu Trp Lys Ile Pro Asn Tyr Gly Ser Ser
        385                 390                 395

ATT ACG GAG GCA ACA CAT CTA GCC CCT TCT GTA TAC CCC CGT GGT TTC   6587
Ile Thr Glu Ala Thr His Leu Ala Pro Ser Val Tyr Pro Pro Gly Phe
400                 405                 410

GGA GAG GTA TTG GTC TTT TTC ATG TCA AAA ATG CCA GGT CCT GGT GCT   6635
Gly Glu Val Leu Val Phe Phe Met Ser Lys Met Pro Gly Pro Gly Ala
415                 420                 425                 430

TAT AAT TTG CCC TGT CTA TTA CCA CAA GAG TAC ATT TCA CAT CTT GCT   6683
Tyr Asn Leu Pro Cys Leu Leu Pro Gln Glu Tyr Ile Ser His Leu Ala
                435                 440                 445

AGT GAA CAA GCC CCT ACT GTA GGT GAG GCT GCC CTG CTC CAC TAT GTT   6731
Ser Glu Gln Ala Pro Thr Val Gly Glu Ala Ala Leu Leu His Tyr Val
        450                 455                 460

GAC CCT GAT ACC GGT CGG AAT CTT GGG GAA TTC AAA GCA TAC CCT GAT   6779
Asp Pro Asp Thr Gly Arg Asn Leu Gly Glu Phe Lys Ala Tyr Pro Asp
        465                 470                 475

GGT TTC CTC ACT TGT GTC CCC AAT GGG GCT AGC TCG GGT CCA CAA CAG   6827
Gly Phe Leu Thr Cys Val Pro Asn Gly Ala Ser Ser Gly Pro Gln Gln
480                 485                 490

CTG CCG ATC AAT GGG GTC TTT GTC TTT GTT TCA TGG GTG TCC AGA TTT   6875
Leu Pro Ile Asn Gly Val Phe Val Phe Val Ser Trp Val Ser Arg Phe
495                 500                 505                 510
```

TABLE 3-continued

The amino acid sequence deduced from nucleotides 5346 through 6935 of the Norwalk virus genome shown in Table 1.

```
TAT CAA TTA AAG CCT GTG GGA ACT GCC AGC TCG GCA AGA GGT AGG CTT     6923
Tyr Gln Leu Lys Pro Val Gly Thr Ala Ser Ser Ala Arg Gly Arg Leu
            515                 520                 525

GGT CTG CGC CGA TAATGCCCA AGCCATAATT GGTGCAATTG CTGCTTCCAC          6975
Gly Leu Arg Arg
            530
```

TABLE 4

The amino acid sequence deduced from nucleotides 6938 through 7573 of the Norwalk virus genome shown in Table 1.

```
CCAGCTCGGC AAGAGGTAGG CTTGGTCTGC GCCGATA ATG GCC CAA GCC ATA ATT    6955
                                        Met Ala Gln Ala Ile Ile
                                        1                       5

GGT GCA ATT GCT GCT TCC ACA GCA GGT AGT GCT CTG GGA GCG GGC ATA     7003
Gly Ala Ile Ala Ala Ser Thr Ala Gly Ser Ala Leu Gly Ala Gly Ile
             10                  15                  20

CAG GTT GGT GGC GAA GCG GCC CTC CAA AGC CAA AGG TAT CAA CAA AAT    7051
Gln Val Gly Gly Glu Ala Ala Leu Gln Ser Gln Arg Tyr Gln Gln Asn
25              30                  35

TTG CAA CTG CAA GAA AAT TCT TTT AAA CAT GAC AGG GAA ATG ATT GGG    7099
Leu Gln Leu Gln Glu Asn Ser Phe Lys His Asp Arg Glu Met Ile Gly
40          45                  50

TAT CAG GTT GAA GCT TCA AAT CAA TTA TTG GCT AAA AAT TTG GCA ACT    7147
Tyr Gln Val Glu Ala Ser Asn Gln Leu Leu Ala Lys Asn Leu Ala Thr
55          60              65              70

AGA TAT TCA CTC CTC CGT GCT GGG GGT TTG ACC AGT GCT CAT GCA GCA    7195
Arg Tyr Ser Leu Leu Arg Ala Gly Gly Leu Thr Ser Ala His Ala Ala
75      80              85

AGA TCT GTG GCA GGA GCT CCA GTC ACC CGC ATT GTA GAT TGG AAT GGC    7243
Arg Ser Val Ala Gly Ala Pro Val Thr Arg Ile Val Asp Trp Asn Gly
90  95              100

GTG AGA GTG TCT GCT CCC GAG TCC TCT GCT ACC ACA TTG AGA TCC GGT    7291
Val Arg Val Ser Ala Pro Glu Ser Ser Ala Thr Thr Leu Arg Ser Gly
105     110             115

GGC TTC ATG TCA GTT CCC ATA CCA TTT GCC TCT AAG CAA AAA CAG GTT    7339
Gly Phe Met Ser Val Pro Ile Pro Phe Ala Ser Lys Gln Lys Gln Val
120 125             130

CAA TCA TCT GGT ATT ACT AAT CCA AAT TAT TCC CCT TCA TCC ATT TCT    7387
Gln Ser Ser Gly Ile Ser Asn Pro Asn Tyr Ser Pro Ser Ser Ile Ser
135 140     145             150

CGA ACC ACT AGT TGG GTC GAG TCA CAA AAC TCA TCG AGA TTT GGA AAT    7435
Arg Thr Thr Ser Trp Val Glu Ser Gln Asn Ser Ser Arg Phe Gly Asn
155     160         165

CTT TCT CCA TAC CAC GCG GAG GCT CTC AAT ACA GTG TGG TTG ACT CCA    7483
Leu Ser Pro Tyr His Ala Glu Ala Leu Asn Thr Val Trp Leu Thr Pro
170 175         180

CCC GGT TCA ACA GCC TCT TCT ACA CTG TCT TCT GTG CCA CGT GGT TAT    7531
Pro Gly Ser Thr Ala Ser Ser Thr Leu Ser Ser Val Pro Arg Gly Tyr
185     190         195

TTC AAT ACA GAC AGG TTG CCA TTA TTC GCA AAT AAT AGG CGA            7573
Phe Asn Thr Asp Arg Leu Pro Leu Phe Ala Asn Asn Arg Arg
200     205         210
```

What is claimed is:

1. A method of inducing an immune response against Norwalk virus in an animal comprising the step of administering to the animal an effective amount of a composition having a purified Norwalk virus immunogen that forms a stable virus-like particle lacking nucleic acids, wherein the immunogen is produced in an expression system using the nucleotide sequence of SEQ. ID. NO.1.

2. The method of claim 1, wherein the immunogen is produced in an expression system using nucleotides 5337 through 7724 of SEQ. ID. NO.1.

3. The method of claim 1, wherein the composition is administered orally.

4. The method of claim 1, wherein the composition is administered parenterally.

5. The method of claim 1, wherein the virus-like particle is non-infectious.

6. The method of claim 3, wherein the composition is administered subsequent to oral administration of sodium bicarbonate.

7. The method of claim 3, wherein the composition is administered prior to oral administration of sodium bicarbonate.

8. The method of claim 3, wherein sodium bicarbonate is administered orally following administration of the composition.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
    (A) LENGTH: 7724 base pairs
    (B) TYPE: nucleic acid
    (C) STRANDEDNESS: single
    (D) TOPOLOGY: unknown (ii) MOLECULE TYPE: cDNA (vi) ORIGINAL SOURCE:
    (A) ORGANISM: Norwalk virus
    (B) STRAIN: 8FIIa
    (C) INDIVIDUAL ISOLATE: 8FIIa (vii) IMMEDIATE SOURCE:
    (B) CLONE: pUCNV-953 and its derivatives (ix) FEATURE:
    (A) NAME/KEY: CDS
    (B) LOCATION: 146..5359
    (D) OTHER INFORMATION: /note= "The protein encoded by
      nucleotides 146 through 5359 is eventually cleaved
      to make at least a picornavirus 2c-like protein, a
      3C-like protease and an RNA-dependent RNA polymerase.

(ix) FEATURE:
    (A) NAME/KEY: CDS
    (B) LOCATION: 5346..6935
    (D) OTHER INFORMATION: /note= "Nucleotides 5346 through
      5359 are used for coding two different amino acid
      sequences: the first is the sequence coded by
      nucleotides 146 through 5359, the second by nucleotides
      5346 through 6935.

(ix) FEATURE:
    (A) NAME/KEY: CDS
    (B) LOCATION: 6938..7573

(xi) SEQUENCE DESCRIPTION: SEQ ID NO: 1:

```
GGCGTCAAAA GACGTCGTTC CTACTGCTGC TAGCAGTGAA AATGCTAACA ACAATAGTAG      60

TATTAAGTCT CGTCTATTGG CGAGACTCAA GGGTTCAGGT GGGGCTACGT CCCCACCCAA     120

CTCGATAAAG ATAACCAACC AAGATATGGC TCTGGGGCTG ATTGGACAGG TCCCAGCGCC     180

AAAGGCCACA TCCGTCGATG TCCCTAAACA ACAGAGGGAT AGACCACCAC GGACTGTTGC     240

CGAAGTTCAA CAAAATTTGC GTTGGACTGA GAGACCACAA GACCAGAATG TTAAGACGTG     300

GGATGAGCTT GACCACACAA CAAAACAACA GATACTTGAT GAACACGCTG AGTGGTTTGA     360

TGCCGGTGGC TTAGGTCCAA GTACACTACC CACTAGTCAT GAACGGTACA CACATGAGAA     420

TGATGAAGGC CACCAGGTAA AGTGGTCGGC TAGGGAAGGT GTAGACCTTG GCATATCCGG     480

GCTCACGACG GTGTCTGGGC TGAGTGGAAT ATGTGCCCG CTACCACCAG TTGACCAAAG      540

GAGCACGACA CCTGCAACTG AGCCCACAAT TGGTGACATG ATCGAATTCT ATGAAGGGCA     600

CATCTATCAT TATGCTATAT ACATAGGTCA AGGCAAGACG GTGGGTGTAC ACTCCCCTCA     660

AGCAGCCTTC TCAATAACGA GGATCACCAT ACAGCCCATA TCAGCTTGGT GGCGAGTCTG     720

TTATGTCCCA CAACCAAAAC AGAGGCTCAC ATACGACCAA CTCAAAGAAT TAGAAAATGA     780

ACCATGGCCG TATGCCGCAG TCACGAACAA CTGCTTCGAA TTTTGTTGCC AGGTCATGTG     840

CTTGGAAGAT ACTTGGTTGC AAAGGAAGCT CATCTCCTCT GGCCGGTTTT ACCACCCGAC     900
```

```
CCAAGATTGG TCCCGAGACA CTCCAGAATT CCAACAAGAC AGCAAGTTAG AGATGGTTAG      960
GGATGCAGTG CTAGCCGCTA TAAATGGGTT GGTGTCGCGG CCATTTAAAG ATCTTCTGGG     1020
TAAGCTCAAA CCCTTGAACG TGCTTAACTT ACTTTCAAAC TGTGATTGGA CGTTCATGGG     1080
GGTCGTGGAG ATGGTGGTCC TCCTTTTAGA ACTCTTTGGA ATCTTTTGGA ACCCACCTGA     1140
TGTTTCCAAC TTTATAGCTT CACTCCTGCC AGATTTCCAT CTACAGGGCC CCGAGGACCT     1200
TGCCAGGGAT CTCGTGCCAA TAGTATTGGG GGGGATCGGC TTAGCCATAG GATTCACCAG     1260
AGACAAGGTA AGTAAGATGA TGAAGAATGC TGTTGATGGA CTTCGTGCGG CAACCCAGCT     1320
CGGTCAATAT GGCCTAGAAA TATTCTCATT ACTAAAGAAG TACTTCTTCG GTGGTGATCA     1380
AACAGAGAAA ACCCTAAAAG ATATTGAGTC AGCAGTTATA GATATGGAAG TACTATCATC     1440
TACATCAGTG ACTCAGCTCG TGAGGGACAA ACAGTCTGCA CGGGCTTATA TGGCCATCTT     1500
AGATAATGAA GAAGAAAAGG CAAGGAAATT ATCTGTCAGG AATGCCGACC CACACGTAGT     1560
ATCCTCTACC AATGCTCTCA TATCCCGGAT CTCAATGGCT AGGGCTGCAT GGCCAAGGC     1620
TCAAGCTGAA ATGACCAGCA GGATGCGTCC TGTGGTCATT ATGATGTGTG GGCCCCCTGG     1680
TATAGGTAAA ACCAAGGCAG CAGAACATCT GGCTAAACGC CTAGCCAATG AGATACGGCC     1740
TGGTGGTAAG GTTGGGCTGG TCCCACGGGA GGCAGTGGAT CATTGGGATG GATATCACGG     1800
AGAGGAAGTG ATGCTGTGGG ACGACTATGG AATGACAAAG ATACAGGAAG ACTGTAATAA     1860
ACTGCAAGCC ATAGCCGACT CAGCCCCCCT AACACTCAAT TGTGACCGAA TAGAAAACAA     1920
GGGAATGCAA TTTGTGTCTG ATGCTATAGT CATCACCACC AATGCTCCTG GCCCAGCCCC     1980
AGTGGACTTT GTCAACCTCG GCCTGTTTG CCGAAGGGTG GACTTCCTTG TGTATTGCAC     2040
GGCACCTGAA GTTGAACACA CGAGGAAAGT CAGTCCTGGG GACACAACTG CACTGAAAGA     2100
CTGCTTCAAG CCCGATTTCT CACATCTAAA AATGGAGTTG GCTCCCCAAG GGGGCTTTGA     2160
TAACCAAGGG AATACCCCGT TTGGTAAGGG TGTGATGAAG CCCACCACCA TAAACAGGCT     2220
GTTAATCCAG GCTGTAGCCT TGACGATGGA GAGACAGGAT GAGTTCCAAC TCCAGGGGCC     2280
TACGTATGAC TTTGATACTG ACAGAGTAGC TGCGTTCACG AGGATGGCCC GAGCCAACGG     2340
GTTGGGTCTC ATATCCATGG CCTCCCTAGG CAAAAAGCTA CGCAGTGTCA CCACTATTGA     2400
AGGATTAAAG AATGCTCTAT CAGGCTATAA AATATCAAAA TGCAGTATAC AATGGCAGTC     2460
AAGGGTGTAC ATTATAGAAT CAGATGGTGC CAGTGTACAA ATCAAAGAAG ACAAGCAAGC     2520
TTTGACCCCT CTGCAGCAGA CAATTAACAC GGCCTCACTT GCCATCACTC GACTCAAAGC     2580
AGCTAGGGCT GTGGCATACG CTTCATGTTT CCAGTCCGCC ATAACTACCA TACTACAAAT     2640
GGCGGGATCT GCGCTCGTTA TTAATCGAGC GGTCAAGCGT ATGTTTGGTA CCCGTACAGC     2700
AGCCATGGCA TTAGAAGGAC CTGGGAAAGA ACATAATTGC AGGGTCCATA AGGCTAAGGA     2760
AGCTGGAAAG GGGCCCATAG GTCATGATGA CATGGTAGAA AGGTTTGGCC TATGTGAAAC     2820
TGAAGAGGAG GAGAGTGAGG ACCAAATTCA AATGGTACCA AGTGATGCCG TCCCAGAAGG     2880
AAAGAACAAA GGCAAGACCA AAAAGGGACG TGGTCGCAAA AATAACTATA ATGCATTCTC     2940
TCGCCGTGGT CTGAGTGATG AAGAATATGA AGAGTACAAA AAGATCAGAG AAGAAAAGAA     3000
TGGCAATTAT AGTATACAAG AATACTTGGA GGACCGCCAA CGATATGAGG AAGAATTAGC     3060
AGAGGTACAG GCAGGTGGTG ATGGTGGCAT AGGAGAAACT GAAATGGAAA TCCGTCACAG     3120
GGTCTTCTAT AAATCCAAGA GTAAGAAACA CCAACAAGAG CAACGGCGAC AACTTGGTCT     3180
AGTGACTGGA TCAGACATCA GAAAACGTAA GCCCATTGAC TGGACCCCGC CAAAGAATGA     3240
ATGGGCAGAT GATGACAGAG AGGTGGATTA TAATGAAAAG ATCAATTTTG AAGCTCCCCC     3300
```

```
GACACTATGG AGCCGAGTCA CAAAGTTTGG ATCAGGATGG GGCTTTTGGG TCAGCCCGAC   3360

AGTGTTCATC ACAACCACAC ATGTAGTGCC AACTGGTGTG AAAGAATTCT TTGGTGAGCC   3420

CCTATCTAGT ATAGCAATCC ACCAAGCAGG TGAGTTCACA CAATTCAGGT TCTCAAAGAA   3480

AATGCGCCCT GACTTGACAG GTATGGTCCT TGAAGAAGGT TGCCCTGAAG GGACAGTCTG   3540

CTCAGTCCTA ATTAAACGGG ATTCGGGTGA ACTACTTCCG CTAGCCGTCC GTATGGGGGC   3600

TATTGCCTCC ATGAGGATAC AGGGTCGGCT TGTCCATGGC CAATCAGGGA TGTTACTGAC   3660

AGGGGCCAAT GCAAAGGGGA TGGATCTTGG CACTATACCA GGAGACTGCG GGCACCATA   3720

CGTCCACAAG CGCGGGAATG ACTGGGTTGT GTGTGGAGTC CACGCTGCAG CCACAAAGTC   3780

AGGCAACACC GTGGTCTGCG CTGTACAGGC TGGAGAGGGC GAAACCGCAC TAGAAGGTGG   3840

AGACAAGGGG CATTATGCCG GCCACGAGAT TGTGAGGTAT GGAAGTGGCC CAGCACTGTC   3900

AACTAAAACA AAATTCTGGA GGTCCTCCCC AGAACCACTG CCCCCGGAG TATATGAGCC    3960

AGCATACCTG GGGGCAAGG ACCCCCGTGT ACAGAATGGC CCATCCCTAC AACAGGTACT    4020

ACGTGACCAA CTGAAACCCT TTGCGGACCC CCGCGGCCGC ATGCCTGAGC CTGGCCTACT   4080

GGAGGCTGCG GTTGAGACTG TAACATCCAT GTTAGAACAG ACAATGGATA CCCCAAGCCC   4140

GTGGTCTTAC GCTGATGCCT GCCAATCTCT TGACAAAACT ACTAGTTCGG GGTACCCTCA   4200

CCATAAAAGG AAGAATGATG ATTGGAATGG CACCACCTTC GTTGGAGAGC TCGGTGAGCA   4260

AGCTGCACAC GCCAACAATA TGTATGAGAA TGCTAAACAT ATGAAACCCA TTTACACTGC   4320

AGCCTTAAAA GATGAACTAG TCAAGCCAGA AAAGATTTAT CAAAAAGTCA AGAAGCGTCT   4380

ACTATGGGGC GCCGATCTCG GAACAGTGGT CAGGGCCGCC CGGGCTTTTG GCCCATTTTG   4440

TGACGCTATA AAATCACATG TCATCAAATT GCCAATAAAA GTTGGCATGA ACACAATAGA   4500

AGATGGCCCC CTCATCTATG CTGAGCATGC TAAATATAAG AATCATTTTG ATGCAGATTA   4560

TACAGCATGG GACTCAACAC AAAATAGACA AATTATGACA GAATCCTTCT CCATTATGTC   4620

GCGCCTTACG GCCTCACCAG AATTGGCCGA GGTTGTGGCC CAAGATTTGC TAGCACCATC   4680

TGAGATGGAT GTAGGTGATT ATGTCATCAG GGTCAAAGAG GGGCTGCCAT CTGGATTCCC   4740

ATGTACTTCC CAGGTGAACA GCATAAATCA CTGGATAATT ACTCTCTGTG CACTGTCTGA   4800

GGCCACTGGT TTATCACCTG ATGTGGTGCA ATCCATGTCA TATTTCTCAT TTTATGGTGA   4860

TGATGAGATT GTGTCAACTG ACATAGATTT TGACCCAGCC CGCCTCACTC AAATTCTCAA   4920

GGAATATGGC CTCAAACCAA CAAGGCCTGA CAAAACAGAA GGACCAATAC AAGTGAGGAA   4980

AAATGTGGAT GGACTGGTCT TCTTGCGGCG CACCATTTCC CGTGATGCGG CAGGGTTCCA   5040

AGGCAGGTTA GATAGGGCTT CGATTGAACG CCAAATCTTC TGGACCCGCG GGCCCAATCA   5100

TTCAGATCCA TCAGAGACTC TAGTGCCACA CACTCAAAGA AAAATACAGT TGATTTCACT   5160

TCTAGGGAA GCTTCACTCC ATGGTGAGAA ATTTTACAGA AAGATTTCCA GCAAGGTCAT   5220

ACATGAAATC AAGACTGGTG GATTGGAAAT GTATGTCCCA GGATGGCAGG CCATGTTCCG   5280

CTGGATGCGC TTCCATGACC TCGGATTGTG GACAGGAGAT CGCGATCTTC TGCCCGAATT   5340

CGTAAATGAT GATGGCGTCT AAGGACGCTA CATCAAGCGT GGATGGCGCT AGTGGCGCTG   5400

GTCAGTTGGT ACCGGAGGTT AATGCTTCTG ACCCTCTTGC AATGGATCCT GTAGCAGGTT   5460

CTTCGACAGC AGTCGCGACT GCTGGACAAG TTAATCCTAT TGATCCCTGG ATAATTAATA   5520

ATTTTGTGCA AGCCCCCCAA GGTGAATTTA CTATTTCCCC AAATAATACC CCCGGTGATG   5580

TTTTGTTTGA TTTGAGTTTG GGTCCCCATC TTAATCCTTT CTTGCTCCAT CTATCACAAA   5640
```

```
TGTATAATGG TTGGGTTGGT AACATGAGAG TCAGGATTAT GCTAGCTGGT AATGCCTTTA      5700

CTGCGGGGAA GATAATAGTT TCCTGCATAC CCCCTGGTTT TGGTTCACAT AATCTTACTA      5760

TAGCACAAGC AACTCTCTTT CCACATGTGA TTGCTGATGT TAGGACTCTA GACCCCATTG      5820

AGGTGCCTTT GGAAGATGTT AGGAATGTTC TCTTTCATAA TAATGATAGA AATCAACAAA      5880

CCATGCGCCT TGTGTGCATG CTGTACACCC CCCTCCGCAC TGGTGGTGGT ACTGGTGATT      5940

CTTTTGTAGT TGCAGGGCGA GTTATGACTT GCCCCAGTCC TGATTTTAAT TTCTTGTTTT      6000

TAGTCCCTCC TACGGTGGAG CAGAAAACCA GGCCCTTCAC ACTCCCAAAT CTGCCATTGA      6060

GTTCTCTGTC TAACTCACGT GCCCCTCTCC CAATCAGTAG TATGGGCATT TCCCCAGACA      6120

ATGTCCAGAG TGTGCAGTTC CAAAATGGTC GGTGTACTCT GGATGGCCGC CTGGTTGGCA      6180

CCACCCCAGT TTCATTGTCA CATGTTGCCA AGATAAGAGG GACCTCCAAT GGCACTGTAA      6240

TCAACCTTAC TGAATTGGAT GGCACACCCT TTCACCCTTT TGAGGGCCCT GCCCCCATTG      6300

GGTTTCCAGA CCTCGGTGGT TGTGATTGGC ATATCAATAT GACACAGTTT GGCCATTCTA      6360

GCCAGACCCA GTATGATGTA GACACCACCC CTGACACTTT TGTCCCCCAT CTTGGTTCAA      6420

TTCAGGCAAA TGGCATTGGC AGTGGTAATT ATGTTGGTGT TCTTAGCTGG ATTTCCCCCC      6480

CATCACACCC GTCTGGCTCC CAAGTTGACC TTTGGAAGAT CCCCAATTAT GGGTCAAGTA      6540

TTACGGAGGC AACACATCTA GCCCCTTCTG TATACCCCCC TGGTTTCGGA GAGGTATTGG      6600

TCTTTTTCAT GTCAAAAATG CCAGGTCCTG GTGCTTATAA TTTGCCCTGT CTATTACCAC      6660

AAGAGTACAT TTCACATCTT GCTAGTGAAC AAGCCCCTAC TGTAGGTGAG GCTGCCCTGC      6720

TCCACTATGT TGACCCTGAT ACCGGTCGGA ATCTTGGGGA ATTCAAAGCA TACCCTGATG      6780

GTTTCCTCAC TTGTGTCCCC AATGGGGCTA GCTCGGGTCC ACAACAGCTG CCGATCAATG      6840

GGGTCTTTGT CTTTGTTTCA TGGGTGTCCA GATTTTATCA ATTAAAGCCT GTGGGAACTG      6900

CCAGCTCGGC AAGAGGTAGG CTTGGTCTGC GCCGATAATG GCCCAAGCCA TAATTGGTGC      6960

AATTGCTGCT TCCACAGCAG GTAGTGCTCT GGGAGCGGGC ATACAGGTTG GTGGCGAAGC      7020

GGCCCTCCAA AGCCAAAGGT ATCAACAAAA TTTGCAACTG CAAGAAAATT CTTTTAAACA      7080

TGACAGGGAA ATGATTGGGT ATCAGGTTGA AGCTTCAAAT CAATTATTGG CTAAAAATTT      7140

GGCAACTAGA TATTCACTCC TCCGTGCTGG GGGTTTGACC AGTGCTGATG CAGCAAGATC      7200

TGTGGCAGGA GCTCCAGTCA CCCGCATTGT AGATTGGAAT GGCGTGAGAG TGTCTGCTCC      7260

CGAGTCCTCT GCTACCACAT TGAGATCCGG TGGCTTCATG TGAGTTCCCA TACCATTTGC      7320

CTCTAAGCAA AAACAGGTTC AATCATCTGG TATTAGTAAT CCAAATTATT CCCCTTCATC      7380

CATTTCTCGA ACCACTAGTT GGGTCGAGTC ACAAAACTCA TCGAGATTTG GAAATCTTTC      7440

TCCATACCAC GCGGAGGCTC TCAATACAGT GTGGTTGACT CCACCCGGTT CAACAGCCTC      7500

TTCTACACTG TCTTCTGTGC CACGTGGTTA TTTCAATACA GACAGGTTGC CATTATTCGC      7560

AAATAATAGG CGATGATGTT GTAATATGAA ATGTGGGCAT CATATTCATT TAATTAGGTT      7620

TAATTAGGTT TAATTTGATG TTAAAAAAAA AAAAAAAAAA AAAAAAAAAA AAAAAAAAAA      7680

AAAAAAAAAA AAAAAAAAAA AAAAAAAAAA AAAAAAAAAA AAAA                      7724
```

(2) INFORMATION FOR SEQ ID NO: 2:

(i) SEQUENCE CHARACTERISTICS:
        (A) LENGTH: 1738 amino acids
        (B) TYPE: amino acid
        (D) TOPOLOGY: linear (ii) MOLECULE TYPE: protein (xi) SEQUENCE DESCRIPTION: SEQ ID NO: 2:

```
Met Ala Leu Gly Leu Ile Gly Gln Val Pro Ala Pro Lys Ala Thr Ser
  1               5                  10                  15

Val Asp Val Pro Lys Gln Gln Arg Asp Arg Pro Pro Arg Thr Val Ala
             20                  25                  30

Glu Val Gln Gln Asn Leu Arg Trp Thr Glu Arg Pro Gln Asp Gln Asn
         35                  40                  45

Val Lys Thr Trp Asp Glu Leu Asp His Thr Thr Lys Gln Gln Ile Leu
     50                  55                  60

Asp Glu His Ala Glu Trp Phe Asp Ala Gly Leu Gly Pro Ser Thr
 65                  70                  75                  80

Leu Pro Thr Ser His Glu Arg Tyr Thr His Glu Asn Asp Glu Gly His
                 85                  90                  95

Gln Val Lys Trp Ser Ala Arg Glu Gly Val Asp Leu Gly Ile Ser Gly
             100                 105                 110

Leu Thr Thr Val Ser Gly Pro Glu Trp Asn Met Cys Pro Leu Pro Pro
         115                 120                 125

Val Asp Gln Arg Ser Thr Thr Pro Ala Thr Glu Pro Thr Ile Gly Asp
 130                 135                 140

Met Ile Glu Phe Tyr Glu Gly His Ile Tyr His Tyr Ala Ile Tyr Ile
145                 150                 155                 160

Gly Gln Gly Lys Thr Val Gly Val His Ser Pro Gln Ala Ala Phe Ser
                 165                 170                 175

Ile Thr Arg Ile Thr Ile Gln Pro Ile Ser Ala Trp Trp Arg Val Cys
             180                 185                 190

Tyr Val Pro Gln Pro Lys Gln Arg Leu Thr Tyr Asp Gln Leu Lys Glu
         195                 200                 205

Leu Glu Asn Glu Pro Trp Pro Tyr Ala Ala Val Thr Asn Asn Cys Phe
     210                 215                 220

Glu Phe Cys Cys Gln Val Met Cys Leu Glu Asp Thr Trp Leu Gln Arg
225                 230                 235                 240

Lys Leu Ile Ser Ser Gly Arg Phe Tyr His Pro Thr Gln Asp Trp Ser
                 245                 250                 255

Arg Asp Thr Pro Glu Phe Gln Gln Asp Ser Lys Leu Glu Met Val Arg
             260                 265                 270

Asp Ala Val Leu Ala Ala Ile Asn Gly Leu Val Ser Arg Pro Phe Lys
         275                 280                 285

Asp Leu Leu Gly Lys Leu Lys Pro Leu Asn Val Leu Asn Leu Leu Ser
     290                 295                 300

Asn Cys Asp Trp Thr Phe Met Gly Val Val Glu Met Val Val Leu Leu
305                 310                 315                 320

Leu Glu Leu Phe Gly Ile Phe Trp Asn Pro Pro Asp Val Ser Asn Phe
                 325                 330                 335

Ile Ala Ser Leu Leu Pro Asp Phe His Leu Gln Gly Pro Glu Asp Leu
             340                 345                 350

Ala Arg Asp Leu Val Pro Ile Val Leu Gly Gly Ile Gly Leu Ala Ile
         355                 360                 365

Gly Phe Thr Arg Asp Lys Val Ser Lys Met Met Lys Asn Ala Val Asp
     370                 375                 380

Gly Leu Arg Ala Ala Thr Gln Leu Gly Gln Tyr Gly Leu Glu Ile Phe
385                 390                 395                 400
```

-continued

```
Ser Leu Leu Lys Lys Tyr Phe Phe Gly Gly Asp Gln Thr Glu Lys Thr
            405                 410                 415
Leu Lys Asp Ile Glu Ser Ala Val Ile Asp Met Glu Val Leu Ser Ser
        420                 425                 430
Thr Ser Val Thr Gln Leu Val Arg Asp Lys Gln Ser Ala Arg Ala Tyr
            435                 440                 445
Met Ala Ile Leu Asp Asn Glu Glu Lys Ala Arg Lys Leu Ser Val
450                 455                 460
Arg Asn Ala Asp Pro His Val Val Ser Thr Asn Ala Leu Ile Ser
465                 470                 475                 480
Arg Ile Ser Met Ala Arg Ala Leu Ala Lys Ala Gln Ala Glu Met
                485                 490                 495
Thr Ser Arg Met Arg Pro Val Val Ile Met Met Cys Gly Pro Pro Gly
            500                 505                 510
Ile Gly Lys Thr Lys Ala Ala Glu His Leu Ala Lys Arg Leu Ala Asn
            515                 520                 525
Glu Ile Arg Pro Gly Gly Lys Val Gly Leu Val Pro Arg Glu Ala Val
        530                 535                 540
Asp His Trp Asp Gly Tyr His Gly Glu Glu Val Met Leu Trp Asp Asp
545                 550                 555                 560
Tyr Gly Met Thr Lys Ile Gln Glu Asp Cys Asn Lys Leu Gln Ala Ile
                565                 570                 575
Ala Asp Ser Ala Pro Leu Thr Leu Asn Cys Asp Arg Ile Glu Asn Lys
            580                 585                 590
Gly Met Gln Phe Val Ser Asp Ala Ile Val Ile Thr Thr Asn Ala Pro
        595                 600                 605
Gly Pro Ala Pro Val Asp Phe Val Asn Leu Gly Pro Val Cys Arg Arg
        610                 615                 620
Val Asp Phe Leu Val Tyr Cys Thr Ala Pro Glu Val Glu His Thr Arg
625                 630                 635                 640
Lys Val Ser Pro Gly Asp Thr Thr Ala Leu Lys Asp Cys Phe Lys Pro
                645                 650                 655
Asp Phe Ser His Leu Lys Met Glu Leu Ala Pro Gln Gly Gly Phe Asp
            660                 665                 670
Asn Gln Gly Asn Thr Pro Phe Gly Lys Gly Val Met Lys Pro Thr Thr
        675                 680                 685
Ile Asn Arg Leu Leu Ile Gln Ala Val Ala Leu Thr Met Glu Arg Gln
        690                 695                 700
Asp Glu Phe Gln Leu Gln Gly Pro Thr Tyr Asp Phe Asp Thr Asp Arg
705                 710                 715                 720
Val Ala Ala Phe Thr Arg Met Ala Arg Ala Asn Gly Leu Gly Leu Ile
                725                 730                 735
Ser Met Ala Ser Leu Gly Lys Lys Leu Arg Ser Val Thr Thr Ile Glu
            740                 745                 750
Gly Leu Lys Asn Ala Leu Ser Gly Tyr Lys Ile Ser Lys Cys Ser Ile
        755                 760                 765
Gln Trp Gln Ser Arg Val Tyr Ile Ile Glu Ser Asp Gly Ala Ser Val
        770                 775                 780
Gln Ile Lys Glu Asp Lys Gln Ala Leu Thr Pro Leu Gln Gln Thr Ile
785                 790                 795                 800
Asn Thr Ala Ser Leu Ala Ile Thr Arg Leu Lys Ala Ala Arg Ala Val
                805                 810                 815
```

```
Ala Tyr Ala Ser Cys Phe Gln Ser Ala Ile Thr Thr Ile Leu Gln Met
            820                 825                 830

Ala Gly Ser Ala Leu Val Ile Asn Arg Ala Val Lys Arg Met Phe Gly
            835                 840                 845

Thr Arg Thr Ala Ala Met Ala Leu Glu Gly Pro Gly Lys Glu His Asn
    850                 855                 860

Cys Arg Val His Lys Ala Lys Glu Ala Gly Lys Gly Pro Ile Gly His
865                 870                 875                 880

Asp Asp Met Val Glu Arg Phe Gly Leu Cys Glu Thr Glu Glu Glu
                885                 890                 895

Ser Glu Asp Gln Ile Gln Met Val Pro Ser Asp Ala Val Pro Glu Gly
            900                 905                 910

Lys Asn Lys Gly Lys Thr Lys Lys Gly Arg Gly Arg Lys Asn Asn Tyr
            915                 920                 925

Asn Ala Phe Ser Arg Arg Gly Leu Ser Asp Glu Glu Tyr Glu Glu Tyr
    930                 935                 940

Lys Lys Ile Arg Glu Glu Lys Asn Gly Asn Tyr Ser Ile Gln Glu Tyr
945                 950                 955                 960

Leu Glu Asp Arg Gln Arg Tyr Glu Glu Glu Leu Ala Glu Val Gln Ala
                965                 970                 975

Gly Gly Asp Gly Gly Ile Gly Glu Thr Glu Met Glu Ile Arg His Arg
            980                 985                 990

Val Phe Tyr Lys Ser Lys Ser Lys His Gln Gln Glu Gln Arg Arg
            995                 1000                1005

Gln Leu Gly Leu Val Thr Gly Ser Asp Ile Arg Lys Arg Lys Pro Ile
    1010                1015                1020

Asp Trp Thr Pro Pro Lys Asn Glu Trp Ala Asp Asp Arg Glu Val
1025                1030                1035                1040

Asp Tyr Asn Glu Lys Ile Asn Phe Glu Ala Pro Pro Thr Leu Trp Ser
                1045                1050                1055

Arg Val Thr Lys Phe Gly Ser Gly Trp Gly Phe Trp Val Ser Pro Thr
                1060                1065                1070

Val Phe Ile Thr Thr Thr His Val Val Pro Thr Gly Val Lys Glu Phe
            1075                1080                1085

Phe Gly Glu Pro Leu Ser Ser Ile Ala Ile His Gln Ala Gly Glu Phe
    1090                1095                1100

Thr Gln Phe Arg Phe Ser Lys Lys Met Arg Pro Asp Leu Thr Gly Met
1105                1110                1115                1120

Val Leu Glu Glu Gly Cys Pro Glu Gly Thr Val Cys Ser Val Leu Ile
                1125                1130                1135

Lys Arg Asp Ser Gly Glu Leu Leu Pro Leu Ala Val Arg Met Gly Ala
            1140                1145                1150

Ile Ala Ser Met Arg Ile Gln Gly Arg Leu Val His Gly Gln Ser Gly
            1155                1160                1165

Met Leu Leu Thr Gly Ala Asn Ala Lys Gly Met Asp Leu Gly Thr Ile
    1170                1175                1180

Pro Gly Asp Cys Gly Ala Pro Tyr Val His Lys Arg Gly Asn Asp Trp
1185                1190                1195                1200

Val Val Cys Gly Val His Ala Ala Ala Thr Lys Ser Gly Asn Thr Val
                1205                1210                1215

Val Cys Ala Val Gln Ala Gly Glu Gly Glu Thr Ala Leu Glu Gly Gly
            1220                1225                1230
```

```
Asp Lys Gly His Tyr Ala Gly His Glu Ile Val Arg Tyr Gly Ser Gly
        1235                1240                1245

Pro Ala Leu Ser Thr Lys Thr Lys Phe Trp Arg Ser Ser Pro Glu Pro
1250                1255                1260

Leu Pro Pro Gly Val Tyr Glu Pro Ala Tyr Leu Gly Gly Lys Asp Pro
1265                1270                1275                1280

Arg Val Gln Asn Gly Pro Ser Leu Gln Gln Val Leu Arg Asp Gln Leu
            1285                1290                1295

Lys Pro Phe Ala Asp Pro Arg Gly Arg Met Pro Glu Pro Gly Leu Leu
        1300                1305                1310

Glu Ala Ala Val Glu Thr Val Thr Ser Met Leu Glu Gln Thr Met Asp
        1315                1320                1325

Thr Pro Ser Pro Trp Ser Tyr Ala Asp Ala Cys Gln Ser Leu Asp Lys
        1330                1335                1340

Thr Thr Ser Ser Gly Tyr Pro His His Lys Arg Lys Asn Asp Asp Trp
1345                1350                1355                1360

Asn Gly Thr Thr Phe Val Gly Glu Leu Gly Glu Gln Ala Ala His Ala
            1365                1370                1375

Asn Asn Met Tyr Glu Asn Ala Lys His Met Lys Pro Ile Tyr Thr Ala
        1380                1385                1390

Ala Leu Lys Asp Glu Leu Val Lys Pro Glu Lys Ile Tyr Gln Lys Val
        1395                1400                1405

Lys Lys Arg Leu Leu Trp Gly Ala Asp Leu Gly Thr Val Val Arg Ala
        1410                1415                1420

Ala Arg Ala Phe Gly Pro Phe Cys Asp Ala Ile Lys Ser His Val Ile
1425                1430                1435                1440

Lys Leu Pro Ile Lys Val Gly Met Asn Thr Ile Glu Asp Gly Pro Leu
            1445                1450                1455

Ile Tyr Ala Glu His Ala Lys Tyr Lys Asn His Phe Asp Ala Asp Tyr
        1460                1465                1470

Thr Ala Trp Asp Ser Thr Gln Asn Arg Gln Ile Met Thr Glu Ser Phe
        1475                1480                1485

Ser Ile Met Ser Arg Leu Thr Ala Ser Pro Glu Leu Ala Glu Val Val
        1490                1495                1500

Ala Gln Asp Leu Leu Ala Pro Ser Glu Met Asp Val Gly Asp Tyr Val
1505                1510                1515                1520

Ile Arg Val Lys Glu Gly Leu Pro Ser Gly Phe Pro Cys Thr Ser Gln
            1525                1530                1535

Val Asn Ser Ile Asn His Trp Ile Ile Thr Leu Cys Ala Leu Ser Glu
        1540                1545                1550

Ala Thr Gly Leu Ser Pro Asp Val Val Gln Ser Met Ser Tyr Phe Ser
        1555                1560                1565

Phe Tyr Gly Asp Asp Glu Ile Val Ser Thr Asp Ile Asp Phe Asp Pro
        1570                1575                1580

Ala Arg Leu Thr Gln Ile Leu Lys Glu Tyr Gly Leu Lys Pro Thr Arg
1585                1590                1595                1600

Pro Asp Lys Thr Glu Gly Pro Ile Gln Val Arg Lys Asn Val Asp Gly
            1605                1610                1615

Leu Val Phe Leu Arg Arg Thr Ile Ser Arg Asp Ala Ala Gly Phe Gln
        1620                1625                1630

Gly Arg Leu Asp Arg Ala Ser Ile Glu Arg Gln Ile Phe Trp Thr Arg
        1635                1640                1645
```

-continued

```
Gly Pro Asn His Ser Asp Pro Ser Glu Thr Leu Val Pro His Thr Gln
    1650                1655                1660

Arg Lys Ile Gln Leu Ile Ser Leu Leu Gly Glu Ala Ser Leu His Gly
1665                1670                1675                1680

Glu Lys Phe Tyr Arg Lys Ile Ser Lys Val Ile His Glu Ile Lys
                1685                1690                1695

Thr Gly Gly Leu Glu Met Tyr Val Pro Gly Trp Gln Ala Met Phe Arg
                1700                1705                1710

Trp Met Arg Phe His Asp Leu Gly Leu Trp Thr Gly Asp Arg Asp Leu
                1715                1720                1725

Leu Pro Glu Phe Val Asn Asp Asp Gly Val
    1730                1735
```

(2) INFORMATION FOR SEQ ID NO: 3:

(i) SEQUENCE CHARACTERISTICS:
        (A) LENGTH: 530 amino acids
        (B) TYPE: amino acid
        (D) TOPOLOGY: linear (ii) MOLECULE TYPE: protein (xi) SEQUENCE DESCRIPTION: SEQ ID NO: 3:

```
Met Met Met Ala Ser Lys Asp Ala Thr Ser Ser Val Asp Gly
 1               5                   10

Ala Ser Gly Ala Gly Gln Leu Val Pro Glu Val Asn Ala Ser Asp Pro
15                  20                  25                  30

Leu Ala Met Asp Pro Val Ala Gly Ser Ser Thr Ala Val Ala Thr Ala
                35                  40                  45

Gly Gln Val Asn Pro Ile Asp Pro Trp Ile Ile Asn Asn Phe Val Gln
                50                  55                  60

Ala Pro Gln Gly Glu Phe Thr Ile Ser Pro Asn Asn Thr Pro Gly Asp
65                  70                  75

Val Leu Phe Asp Leu Ser Leu Gly Pro His Leu Asn Pro Phe Leu Leu
    80                  85                  90

His Leu Ser Gln Met Tyr Asn Gly Trp Val Gly Asn Met Arg Val Arg
95                  100                 105                 110

Ile Met Leu Ala Gly Asn Ala Phe Thr Ala Gly Lys Ile Ile Val Ser
                115                 120                 125

Cys Ile Pro Pro Gly Phe Gly Ser His Asn Leu Thr Ile Ala Gln Ala
                130                 135                 140

Thr Leu Phe Pro His Val Ile Ala Asp Val Arg Thr Leu Asp Pro Ile
                145                 150                 155

Glu Val Pro Leu Glu Asp Val Arg Asn Val Leu Phe His Asn Asn Asp
                160                 165                 170

Arg Asn Gln Gln Thr Met Arg Leu Val Cys Met Leu Tyr Thr Pro Leu
175                 180                 185                 190

Arg Thr Gly Gly Gly Thr Gly Asp Ser Phe Val Val Ala Gly Arg Val
                195                 200                 205

Met Thr Cys Pro Ser Pro Asp Phe Asn Phe Leu Phe Leu Val Pro Pro
                210                 215                 220

Thr Val Glu Gln Lys Thr Arg Pro Phe Thr Leu Pro Asn Leu Pro Leu
                225                 230                 235

Ser Ser Leu Ser Asn Ser Arg Ala Pro Leu Pro Ile Ser Ser Met Gly
240                 245                 250
```

```
Ile Ser Pro Asp Asn Val Gln Ser Val Gln Phe Gln Asn Gly Arg Cys
255                 260                 265                 270

Thr Leu Asp Gly Arg Leu Val Gly Thr Thr Pro Val Ser Leu Ser His
            275                 280                 285

Val Ala Lys Ile Arg Gly Thr Ser Asn Gly Thr Val Ile Asn Leu Thr
            290                 295                 300

Glu Leu Asp Gly Thr Pro Phe His Pro Phe Glu Gly Pro Ala Pro Ile
            305                 310                 315

Gly Phe Pro Asp Leu Gly Gly Cys Asp Trp His Ile Asn Met Thr Gln
            320                 325                 330

Phe Gly His Ser Ser Gln Thr Gln Tyr Asp Val Asp Thr Thr Pro Asp
335                 340                 345                 350

Thr Phe Val Pro His Leu Gly Ser Ile Gln Ala Asn Gly Ile Gly Ser
                355                 360                 365

Gly Asn Tyr Val Gly Val Leu Ser Trp Ile Ser Pro Ser His Pro
                370                 375                 380

Ser Gly Ser Gln Val Asp Leu Trp Lys Ile Pro Asn Tyr Gly Ser Ser
            385                 390                 395

Ile Thr Glu Ala Thr His Leu Ala Pro Ser Val Tyr Pro Pro Gly Phe
            400                 405                 410

Gly Glu Val Leu Val Phe Phe Met Ser Lys Met Pro Gly Pro Gly Ala
415                 420                 425                 430

Tyr Asn Leu Pro Cys Leu Leu Pro Gln Glu Tyr Ile Ser His Leu Ala
                435                 440                 445

Ser Glu Gln Ala Pro Thr Val Gly Glu Ala Ala Leu Leu His Tyr Val
            450                 455                 460

Asp Pro Asp Thr Gly Arg Asn Leu Gly Glu Phe Lys Ala Tyr Pro Asp
            465                 470                 475

Gly Phe Leu Thr Cys Val Pro Asn Gly Ala Ser Ser Gly Pro Gln Gln
            480                 485                 490

Leu Pro Ile Asn Gly Val Phe Val Phe Val Ser Trp Val Ser Arg Phe
495                 500                 505                 510

Tyr Gln Leu Lys Pro Val Gly Thr Ala Ser Ser Ala Arg Gly Arg Leu
                515                 520                 525

Gly Leu Arg Arg
            530

(2) INFORMATION FOR SEQ ID NO: 4:

(i) SEQUENCE CHARACTERISTICS:
        (A) LENGTH: 212 amino acids
        (B) TYPE: amino acid
        (D) TOPOLOGY: linear (ii) MOLECULE TYPE: protein (xi) SEQUENCE DESCRIPTION: SEQ ID NO: 4:

Met Ala Gln Ala Ile Ile
1               5

Gly Ala Ile Ala Ala Ser Thr Ala Gly Ser Ala Leu Gly Ala Gly Ile
            10                  15                  20

Gln Val Gly Gly Glu Ala Ala Leu Gln Ser Gln Arg Tyr Gln Gln Asn
            25                  30                  35

Leu Gln Leu Gln Glu Asn Ser Phe Lys His Asp Arg Glu Met Ile Gly
        40                  45                  50
```

-continued

```
Tyr Gln Val Glu Ala Ser Asn Gln Leu Leu Ala Lys Asn Leu Ala Thr
 55              60                  65                  70

Arg Tyr Ser Leu Leu Arg Ala Gly Gly Leu Thr Ser Ala Asp Ala Ala
             75                  80                  85

Arg Ser Val Ala Gly Ala Pro Val Thr Arg Ile Val Asp Trp Asn Gly
             90                  95                 100

Val Arg Val Ser Ala Pro Glu Ser Ser Ala Thr Thr Leu Arg Ser Gly
            105                 110                 115

Gly Phe Met Ser Val Pro Ile Pro Phe Ala Ser Lys Gln Lys Gln Val
            120             125                 130

Gln Ser Ser Gly Ile Ser Asn Pro Asn Tyr Ser Pro Ser Ser Ile Ser
135                 140                 145                 150

Arg Thr Thr Ser Trp Val Glu Ser Gln Asn Ser Ser Arg Phe Gly Asn
             155                 160                 165

Leu Ser Pro Tyr His Ala Glu Ala Leu Asn Thr Val Trp Leu Thr Pro
            170                 175                 180

Pro Gly Ser Thr Ala Ser Ser Thr Leu Ser Ser Val Pro Arg Gly Tyr
        185                 190                 195

Phe Asn Thr Asp Arg Leu Pro Leu Phe Ala Asn Asn Arg Arg
200                 205                 210
```